(12) United States Patent
Lanza et al.

(10) Patent No.: US 9,750,241 B2
(45) Date of Patent: Sep. 5, 2017

(54) BLOOD SUBSTITUTE COMPOSITION AND METHOD OF USE

(71) Applicant: WASHINGTON UNIVERSITY, St. Louis, MO (US)

(72) Inventors: Gregory M. Lanza, St. Louis, MO (US); Dipanjan Pan, St. Louis, MO (US); Allan Doctor, St. Louis, MO (US); Philip C. Spinella, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 15/460,843

(22) Filed: Mar. 16, 2017

(65) Prior Publication Data

US 2017/0181424 A1 Jun. 29, 2017

Related U.S. Application Data

(63) Continuation of application No. 15/232,298, filed on Aug. 9, 2016, which is a continuation of application No. 14/930,396, filed on Nov. 2, 2015, now Pat. No. 9,486,508, which is a continuation-in-part of application No. PCT/US2014/036762, filed on May 5, 2014.

(60) Provisional application No. 61/819,426, filed on May 3, 2013.

(51) Int. Cl.

| A61K 31/70 | (2006.01) |
| A61K 9/16 | (2006.01) |
| A61K 49/00 | (2006.01) |
| A61K 38/41 | (2006.01) |
| A61K 31/519 | (2006.01) |
| A61K 31/44 | (2006.01) |
| A61K 31/355 | (2006.01) |
| B23B 5/16 | (2006.01) |
| A01N 1/02 | (2006.01) |

(52) U.S. Cl.
CPC .................. *A01N 1/0226* (2013.01)

(58) Field of Classification Search
None
See application file for complete search history.

(56) References Cited

U.S. PATENT DOCUMENTS

| 9,486,508 B2 | 11/2016 | Lanza et al. |
| 2016/0051635 A1 | 2/2016 | Lanza et al. |
| 2016/0346358 A1 | 12/2016 | Lanza et al. |

FOREIGN PATENT DOCUMENTS

| WO | 2009049089 A1 | 4/2009 |
| WO | 2011133635 A2 | 10/2011 |
| WO | 2014179793 A1 | 11/2014 |

OTHER PUBLICATIONS

Bonaventura, C. et al., "Molecular Controls of the Oxygenation and Redox Reactions of Hemoglobin," Antioxidants & Redox Signaling, 2013, pp. 2298-2313, vol. 18, No. 17.
Chang, T., "From artificial red blood cells, oxygen carriers, and oxygen therapeutics to artificial cells, nanomedicine, and beyond," PubMed Central Canada Author Manuscript, pp. 1-6, Artificial Cells, Blood Substitutes, and Immobilization Biotechnology, Jun. 2012, pp. 197-199, vol. 40, No. 3.
Doctor, A. et al., "Hemoglobin conformation couples erythrocyte S-nitrosothiol content to O2 gradients," PNAS, Apr. 19, 2005, pp. 5709-5714, vol. 102, No. 16.
Extended European Search Report dated Nov. 25, 2016 from related European Patent Application No. 14791114.3; 8 pgs.
Gravitz, L., "Artificial Red Blood Cells for Delivery," MIT Technology Review, Dec. 15, 2009, 4 pgs., retrieved on Nov. 15, 2016 from https://www.technologyreview.com/s/416687/artificial-red-blood-cells-for-drug-delivery/.
International Search Report and Written Opinion dated Oct. 9, 2014 from related International Application No. PCT/US2014/36762; 7 pgs.
Mozzarelli, A. et al., "Haemoglobin-based oxygen carriers: research and reality towards an alternative to blood transfusions," Blood Transfus., 2010, pp. s59-s68, vol. 8, Supplement 3.
Notice of Allowance dated Sep. 16, 2016 from related U.S. Appl. No. 15/232,298; 11 pgs.
Notice of Allowance dated Dec. 19, 2016 from related U.S. Appl. No. 15/232,298; 6 pgs.
Pan, D. et al., "Ligand-Directed Nanobialys as Theranostic Agent for Drug Delivery and Manganese-Based Magnetic Resonance Imaging of Vascular Targets," NIH Public Access Author Manuscript, Aug. 14, 2009, pp. 1-7; J. Am. Chem. Soc., Jul. 23, 2008, pp. 9186-9187, vol. 130, No. 29.
Piras, A. et al., "Polymeric nanoparticles for hemoglobin-based oxygen carriers," Biochimica et Biophysica Acta, 2008, pp. 1454-1461, vol. 1784.
Rogers, S. et al., "Hypoxia limits antioxidant capacity in red blood cells by altering glycolytic pathway dominance," FASEB J., Sep. 2009, pp. 3159-3170, vol. 23, No. 9.
Safran, M. et al., "Mouse model for noninvasive imaging of HIF prolyl hydroxylase activity: Assessment of an oral agent that stimulates erythropoietin production," PNAS, Jan. 3, 2006, pp. 105-110, vol. 103, No. 1.
Tsui et al., "Priming of hypoxia-inducible factor by neuronal nitric oxide synthase is essential for adaptive responses to severe anemia," PNAS, Oct. 18, 2011, pp. 17544-17549, vol. 108, No. 42.
Vindico Nanobiotechnology, Inc., Abstract of Project Number1R43HL103388-01 entitled "Fully Biodegradable Polymersome-Encapsulated Hemoglobin as a Novel Nanoparticle-B," NIH RePORTER, NIH Research Portfolio Online Reporting Tools Expenditures and Results, accessed Mar. 28, 2016, pp. 1-2.
Zhao, M. et al., "Alveolar macrophage activation is a key initiation signal for acute lung ischemia-reperfusion injury," AJP—Lung Cellular and Olecular Physiology, 2006, pp. L1018-L1026, vol. 291.

*Primary Examiner* — Jeffrey T Palenik
(74) *Attorney, Agent, or Firm* — Polsinelli PC

(57) ABSTRACT

The present disclosure provides oxygen-carrying nanoparticles, methods of making the nanoparticles, and methods of using the nanoparticles to carry oxygen in blood.

10 Claims, 20 Drawing Sheets
(14 of 20 Drawing Sheet(s) Filed in Color)

BLOOD SUBSTITUTE COMPOSITION AND METHOD OF USE

CROSS REFERENCE TO RELATED APPLICATIONS

This application claims the priority of U.S. Ser. No. 15/232,298, filed, Aug. 9, 2016, which is a continuation of U.S. Ser. No. 14/930,396, filed Nov. 2, 2015, which claims the priority of PCT Application PCT/US2014/036762, filed May 5, 2014, which claims the benefit of U.S. provisional application No. 61/819,426, filed May 3, 2013, each of which is hereby incorporated by reference in its entirety.

GOVERNMENTAL RIGHTS

This invention was made with government support under HL094470 and NS073457 awarded by National Institutes of Health. The government has certain rights in the invention.

FIELD OF THE INVENTION

The present disclosure generally relates to nanoparticles comprising an oxygen-carrying composition, methods of making the nanoparticles, and methods of using the nanoparticles to carry oxygen in blood.

BACKGROUND OF THE INVENTION

Blood transfusions are life-saving procedures used in medical conditions and emergencies to replace lost components of the blood. According to the American Red Cross, someone in the U.S. needs blood every two seconds, more than 44,000 blood donations are needed every day, and a total of 30 million blood components are transfused each year in the U.S. A single car accident victim can require as many as 100 pints of blood. In addition, patients with diseases such as sickle cell anemia and cancer affect millions of people in the U.S., and patients with these diseases can require frequent blood transfusions throughout their lives. Major worldwide blood shortages, infected donated blood, the necessity for blood typing, a short shelf life of stored blood, and the inadequacy of stored blood for use in certain situations such as battlefield scenarios and trauma, have led scientists to synthesize and test blood substitute products. Although non-blood volume expanders for cases where only volume restoration is required are widely available, to date there is no well accepted oxygen-carrying blood substitutes. Perfluorocarbon based oxygen-carrying products rely on dissolved oxygen, dissolve 3 times more in oxygen than red blood cells, and have a long shelf life. However, PFC-based products have failed due to poor oxygen delivery functionality, short half-life in circulation, complement activation by pluronic surfactants in PFC-based products, and require cold storage at freezing temperatures. On the other hand, currently available hemoglobin based oxygen carriers (HBOCs) have a short period of functionality during circulation, have poor oxygen capture and release dynamics, and are incompatible with dry storage, limiting their use in remote areas. In addition, hemoglobin based oxygen carriers have been shown to be unsafe, causing hemodynamic and gastrointestinal perturbations related to nitric oxide (NO) scavenging, free radical induction, and alteration of biochemical and hematological parameters such as increased liver enzyme levels and platelet aggregation.

Therefore, there is a need for a safe and efficient oxygen-carrying blood substitute having adequate oxygen capture and release dynamics that does not interfere with normal regulation of blood vessel caliber, is capable of maintaining oxygen-carrying functionality during circulation, and is amenable to extended storage and ease of use.

SUMMARY OF THE INVENTION

Accordingly, in one aspect, the present disclosure provides an oxygen-carrying nanoparticle. The nanoparticle has a substantially bi-concaved disc shape, comprises an aqueous core and a shell comprising an amphiphilic polymer. The nanoparticle also comprises an oxygen-carrying agent, an allosteric effector, and a reducing agent. The amphiphilic polymer may comprise a branched polymer conjugated to a lipid. The surface of the amphiphilic polymer comprising the outer layer of the shell may be derivatized with polyethylene glycol. The average diameter of the nanoparticle may be from about 150 nm to about 300 nm, and the average height of the nanoparticle is from about 30 nm to about 80 nm. The nanoparticle may comprise a through-hole or a depression. The amphiphilic polymer may comprise polyethyleneimine conjugated to C24-pentacosadiynoic acid. The amphiphilic polymer may also comprise polyethyleneimine conjugated to palmitic acid. The oxygen-carrying agent may be hemoglobin. The allosteric effector may be 2,3-DPG. The reducing agent may be leucomethylene blue. The nanoparticle may comprise about 20% to about 60% (w/v) hemoglobin. The nanoparticle may be lyophilizeable and stored for extended periods at ambient conditions. The lyophilized nanoparticles may be reconstituted in an aqueous buffer at various concentrations prior to administration. The nanoparticle may not substantially sequester nitric oxide. The nanoparticle may limit the oxidation of hemoglobin to about 10% or less of the total concentration of hemoglobin in the nanoparticle.

In another aspect, the present disclosure provides a process for the preparation of an oxygen-carrying nanoparticle. The nanoparticle has a substantially bi-concaved disc shape, comprises an aqueous core and a shell comprising an amphiphilic polymer. The nanoparticle also comprises an oxygen-carrying agent, an allosteric effector, and a reducing agent. The process comprises hydrophobically modifying a branched polymer by covalently linking lipids to free reactive groups of the polymer to form an amphiphilic polymer. The amphiphilic polymer is then mixed with a non-polar solvent. The mixture is agitated to form a plurality of inverted micelles comprising the amphiphilic polymer. The inverted micelles are then agitated in the presence of heat and an aqueous solvent to form the bi-concaved disc shaped nanoparticles. The oxygen-carrying agent, the allosteric effector, and the reducing agent are added to the nanoparticles and the mixture is agitated to load the oxygen-carrying agent, the allosteric effector, and the reducing agent into the nanoparticles. The oxygen-carrying agent, the allosteric effector, and the reducing agent may be contained within the aqueous inner core of the nanoparticle.

In another aspect, the present disclosure provides a process for the preparation of an oxygen-carrying nanoparticle. The nanoparticle has a substantially bi-concaved disc shape, comprises an aqueous core and a shell comprising an amphiphilic polymer. The nanoparticle also comprises an oxygen-carrying agent, an allosteric effector, and a reducing agent. The process comprises hydrophobically modifying a branched polymer by covalently linking lipids to free reactive groups of the polymer to form an amphiphilic polymer. The amphiphilic polymer is then mixed with a non-polar solvent. The mixture is agitated to form a plurality of inverted micelles comprising the amphiphilic polymer. The inverted micelles are then agitated in the presence of heat and an aqueous solvent to form the bi-concaved disc shaped nanoparticles. The oxygen-carrying agent, the allosteric effector, and the reducing agent are added to the nanoparticles and the mixture is agitated to load the oxygen-carrying agent, the allosteric effector, and the reducing agent into the nanoparticles. The oxygen-carrying agent, the allosteric effector, and the reducing agent may be contained within the aqueous inner core of the nanoparticle.

In yet another aspect, the present disclosure provides a blood substitute composition. The composition comprises an oxygen-carrying nanoparticle. The nanoparticle has a substantially bi-concaved disc shape, comprises an aqueous core and a shell comprising an amphiphilic polymer. The nanoparticle also comprises an oxygen-carrying agent, an allosteric effector, and a reducing agent. The blood substitute composition may comprise from about $4 \times 10^{12}$ to about $4 \times 10^{13}$ nanoparticles/ml. The blood substitute may be reconstituted in a fashion that is tailored to the status of a patient's circulating blood volume; the blood substitute may be composed in a more concentrated fashion to be administered to normovolemic subjects (e.g. a subject with anemia) or in a more dilute fashion to be administered to hypovolemic patients (e.g. a subject with hemorrhage).

In another aspect, the present disclosure provides a method of supplementing the oxygen-carrying capacity of a subject's blood. The method comprises, administering to the subject an effective amount of an oxygen-carrying nanoparticle. The nanoparticle has a substantially bi-concaved disc shape, comprises an aqueous core and a shell comprising an amphiphilic polymer. The nanoparticle also comprises an oxygen-carrying agent, an allosteric effector, and a reducing agent. When administered to subjects with symptomatic anemia or hemorrhage, the administered nanoparticle will capture $O_2$ during perfusion through the lungs and subsequently, deliver $O_2$ to tissue during systemic perfusion. $O_2$ delivery to tissue by the nanoparticle will be enabled by the following key nanoparticle design features: (1) The nanoparticle shell prevents trapping of nitric oxide by an oxygen carrying agent (e.g. hemoglobin, modified hemoglobin, leghemoglobin, hemin, or others) permitting endogenous signaling that normally routes blood flow to areas of $O_2$ delivery lack. (2) The nanoparticle payload contains an heterotropic allosteric effector molecule (e.g. 2,3-DPG or others), which modifies the oxygen carrying agent's $O_2$ affinity; the free concentration of the allosteric effector in the particle core is modulated by pH-responsive binding to the nanoparticle inner shell—so that the allosteric effector is sequestered to the inner shell during lung perfusion (at high pH, thereby increasing the oxygen carrying agent's $O_2$ affinity and facilitating $O_2$ capture) and the allosteric effector oxygen carrying agent's is released from the inner shell during systemic perfusion (low pH, thereby lowering the oxygen carrying agent's $O_2$ affinity and facilitating $O_2$ release). This effect is amplified in settings of physiologic need [with lung pathology, hyperventilation raises pH and enhances $O_2$ capture; with tissue hypoxia, anaerobic metabolism lowers pH and enhances $O_2$ release]. (3) The nanoparticle payload contains a reducing agent (e.g. leucomethylene blue, glutathioine, ascorbate or others) which recycles oxidized oxygen carrying agent, extending effective circulating time for the nanoparticle. Thereby the nanoparticle will effectively release $O_2$ during perfusion across the $O_2$ tensions/gradients encountered in normal/abnormal physiology (e.g. in a human, tissue $pO_2$ ranges from 40 to 5 Torr).

In an additional aspect, the present disclosure provides a method for conducting the administration of an oxygen carrying nanoparticle into a subject. The method comprises transfusing a solution comprising an oxygen-carrying nanoparticle into the subject. The nanoparticle has a substantially bi-concaved disc shape, comprises an aqueous core and a shell comprising an amphiphilic polymer. The nanoparticle also comprises an oxygen-carrying agent, an allosteric effector, and a reducing agent.

In another aspect, the present disclosure provides a method of supplementing the oxygen-carrying capacity of a subject's blood. The method comprises, administering to the subject an effective amount of an oxygen-carrying nanoparticle. The nanoparticle has a substantially bi-concaved disc shape, comprises an aqueous inner core and a hydrophilic outer shell comprising an amphiphilic polymer. The nanoparticle also comprises hemoglobin or synthetic hemoglobin, 2,3-DPG, and leucomethylene blue. When administered to subjects with symptomatic anemia or hemorrhage, the administered nanoparticle will capture $O_2$ during perfusion through the lungs and subsequently, deliver $O_2$ to tissue during systemic perfusion. $O_2$ delivery to tissue by the nanoparticle will be enabled by the following key nanoparticle design features: (1) The nanoparticle shell prevents trapping of nitric oxide by hemoglobin or synthetic hemoglobin, permitting endogenous signaling that normally routes blood flow to areas of $O_2$ delivery lack. (2) The nanoparticle payload contains 2,3-DPG, which modifies Hb $O_2$ affinity; the free concentration of 2,3-DPG in the particle core is modulated by pH-responsive binding to the nanoparticle inner shell—so that 2,3,-DPG is sequestered to the inner shell during lung perfusion (at high pH, thereby increasing $HbO_2$ affinity and facilitating $O_2$ capture) and 2,3-DPG is released from the inner shell during systemic perfusion (low pH, thereby lowering $HbO_2$ affinity and facilitating $O_2$ release). This effect is amplified in settings of physiologic need [with lung pathology, hyperventilation raises pH and enhances $O_2$ capture; with tissue hypoxia, anaerobic metabolism lowers pH and enhances $O_2$ release]. (3) The nanoparticle payload contains leucomethylene blue which recycles oxidized Hb, extending effective circulating time for the nanoparticle. Thereby the nanoparticle will effectively release $O_2$ during perfusion across the $O_2$ tensions/gradients encountered in normal/abnormal physiology (e.g. in a human, tissue $pO_2$ ranges from 40 to 5 Torr).

DESCRIPTION OF THE FIGURES

The application file contains at least one photograph executed in color. Copies of this patent application publication with color photographs will be provided by the Office upon request and payment of the necessary fee.

(red curves). (A) Oxygen binding-dissociation curves of oxygen-carrying nanoparticles labeled with leucobenzyl methylene blue. (B) Oxygen binding-dissociation curves of the oxygen-carrying nanoparticles in (A) after about five days in storage. (C) Oxygen binding-dissociation curves of unlabeled oxygen-carrying nanoparticles. (D) Oxygen binding-dissociation curves of the unlabeled oxygen-carrying nanoparticles in (C) after about five days in storage.

Figure 3A:
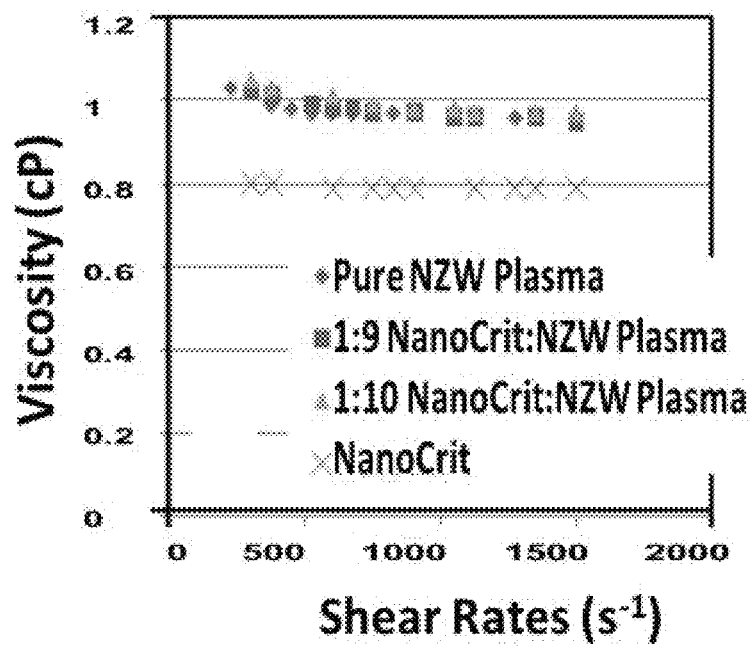
Figure 3B:
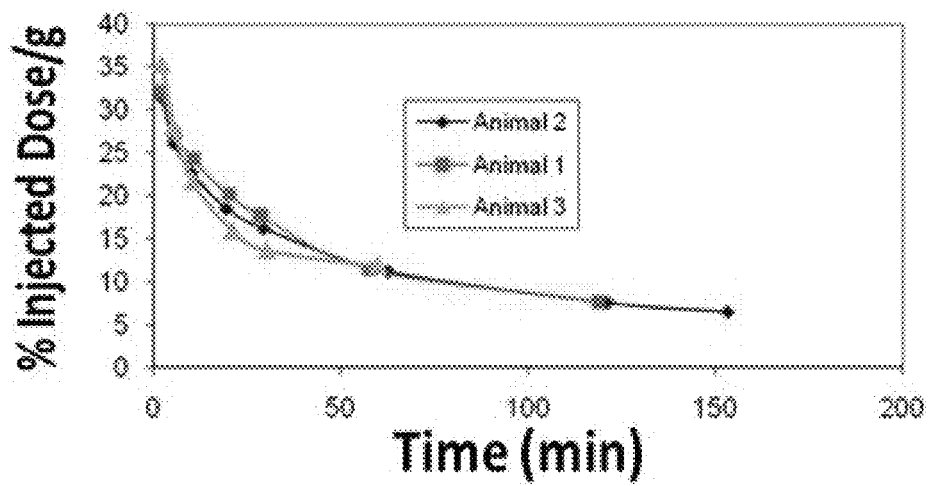

FIG. 3A-B depicts graphs showing the rheological properties (A) and pharmacokinetic profile (B) of a nanoparticle. (A) Nanoparticle:plasma suspensions of 1:9 and 1:10 in volumetric ratio to NZW (rabbit) plasma were studied at 37.1° C. using data points corresponding to at least 10% torque (Wells-Brookfield Cone/Plate Viscometer). The viscosity against shear rate plots revealed the nanoparticles had no effect on the plasma viscosity. (B) Nanoparticle hemoglobin was radiolabeled with a $^{99m}$Tc tracer dose (50 pCi/kg) and administered to rats (n=3). Blood samples were drawn at 0, 5, 20, 40, 60, 90, 120, 150, minutes post administration into heparinized micro capillary tubes, sealed, and 10 µl aliquots drawn into a micro syringe was placed in plastic tubes, capped, and counted using an automated well gamma counter (Perkin-Elmer, Wizard 3). Findings illustrate bi-exponential clearance typical for nanoparticles of this particular size range.

Figure 4:
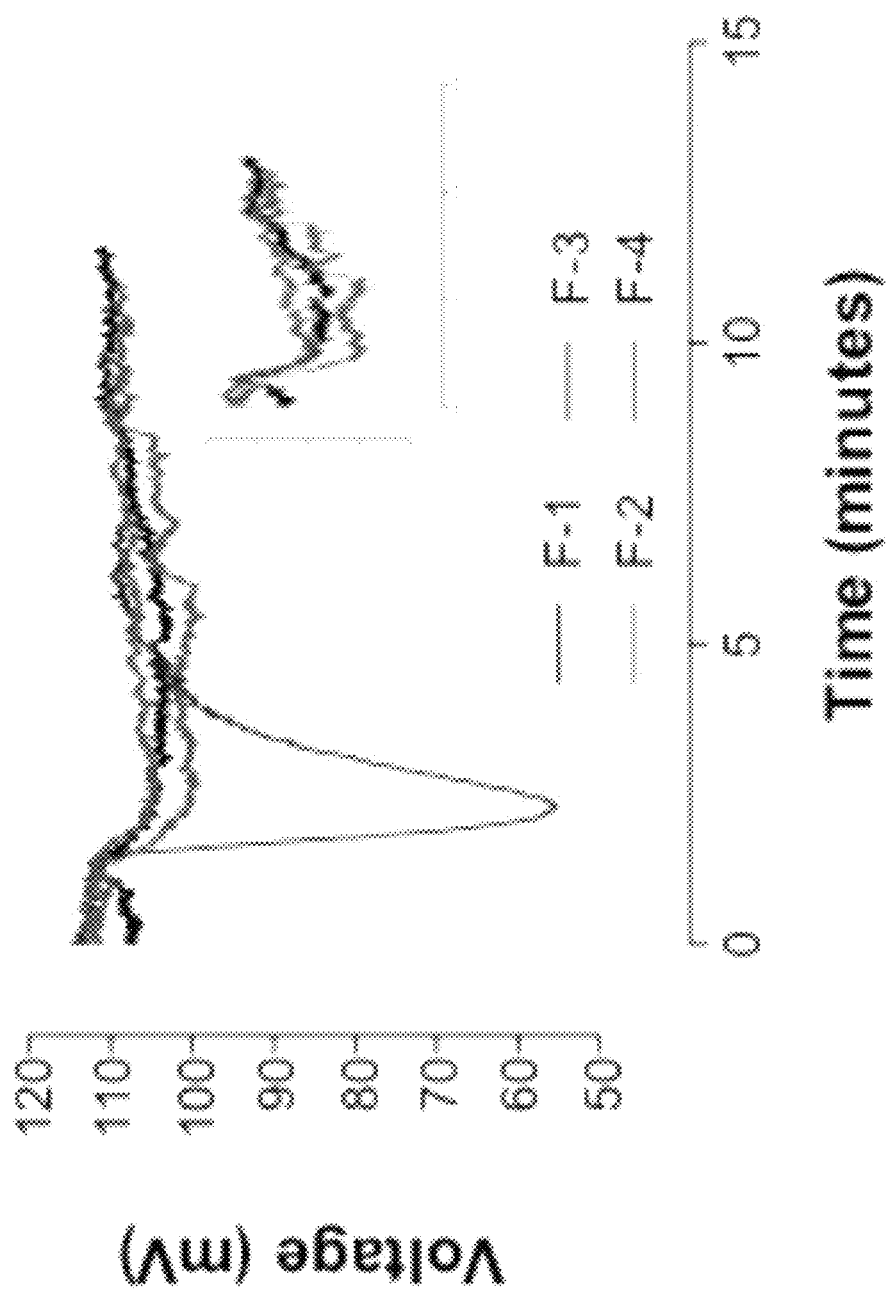

FIG. 4 graphically depicts representative traces from an NO sequestration assay of the four different nanoparticle formulations described in Table 2. Inset, sample F-3 has been excluded, to give a clearer picture of other responses. Sample injections are equimolar for heme, data are normalized to permit overlapping.

Figure 5:
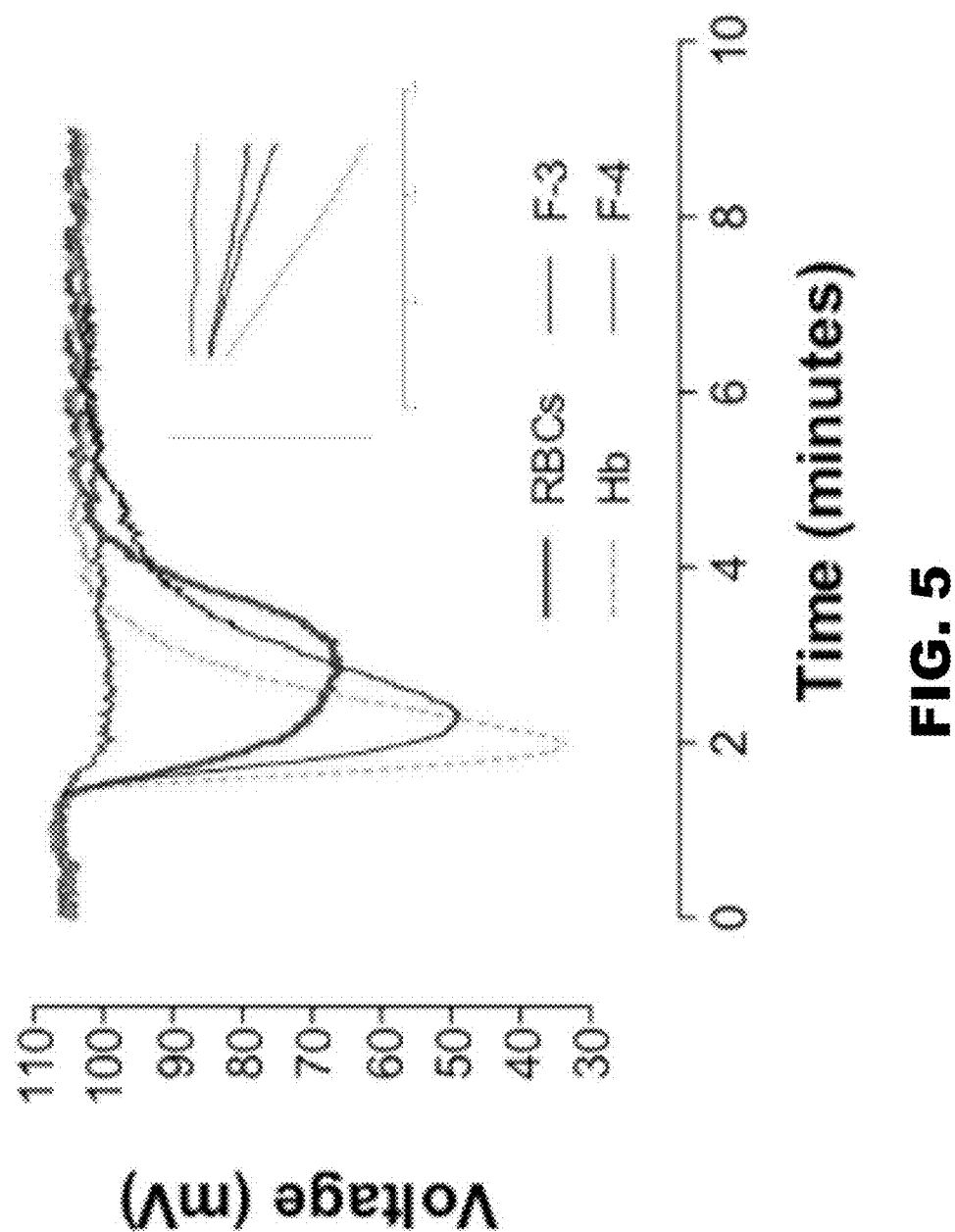

FIG. 5 graphically depicts representative traces from an NO sequestration assay of RBCs, cell-free Hb and two different nanoparticle formulations, F-3 and F-4 (see Table 2). Samples are equimolar for heme. Data are normalized to permit overlapping. Inset: Initial sequestration rate for each sample (trend lines fitted to the first 10 seconds of data).

Figure 6:
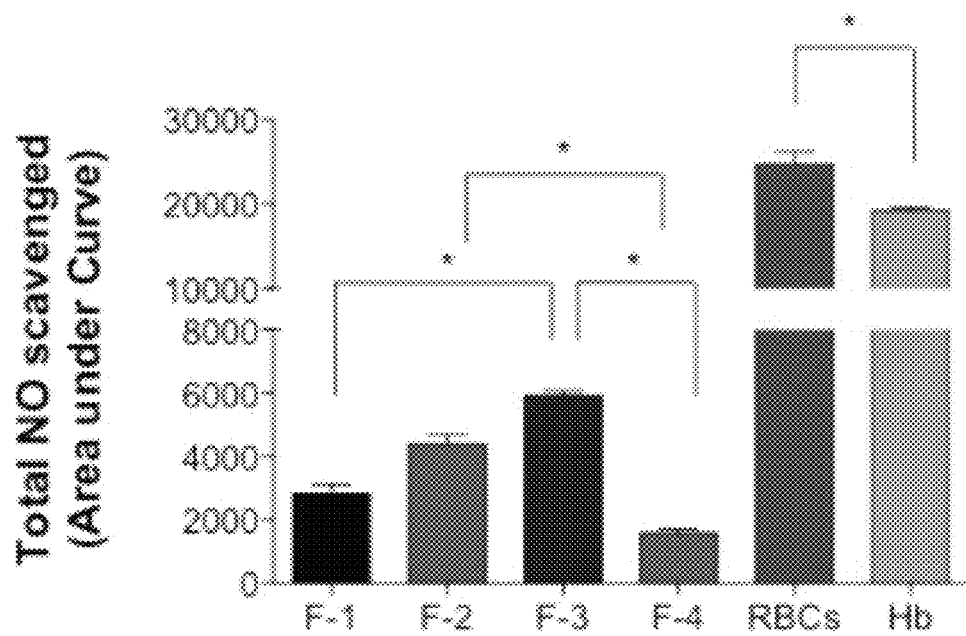

FIG. 6 is a bar graph depicting the total NO scavenged for four nanoparticle formulations (F-1, F-2, F-3, and F-4; see Table 2) in comparison to physiological controls (RBCs and cell-free Hb). Total area under curve (AUC) represents total NO sequestered. All samples are equimolar for heme. * p<0.05; one way ANOVA (n=5). All nanoparticle formulations differ from RBC and Hb samples.

Figure 7:
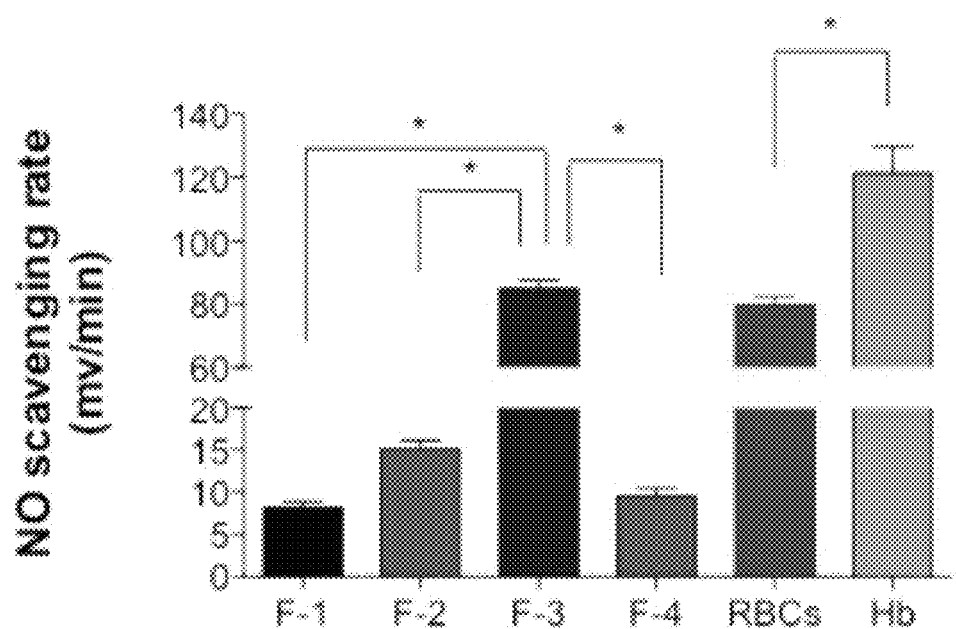
Figure 8A:
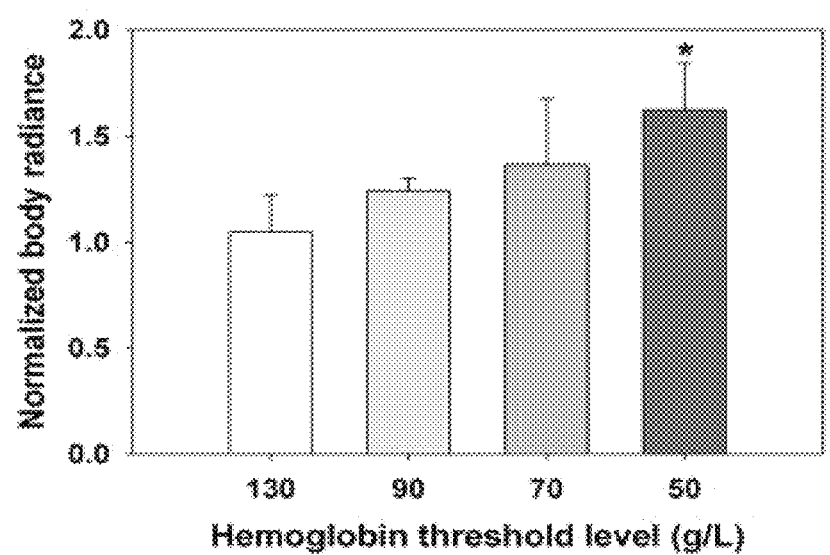
Figure 8B:
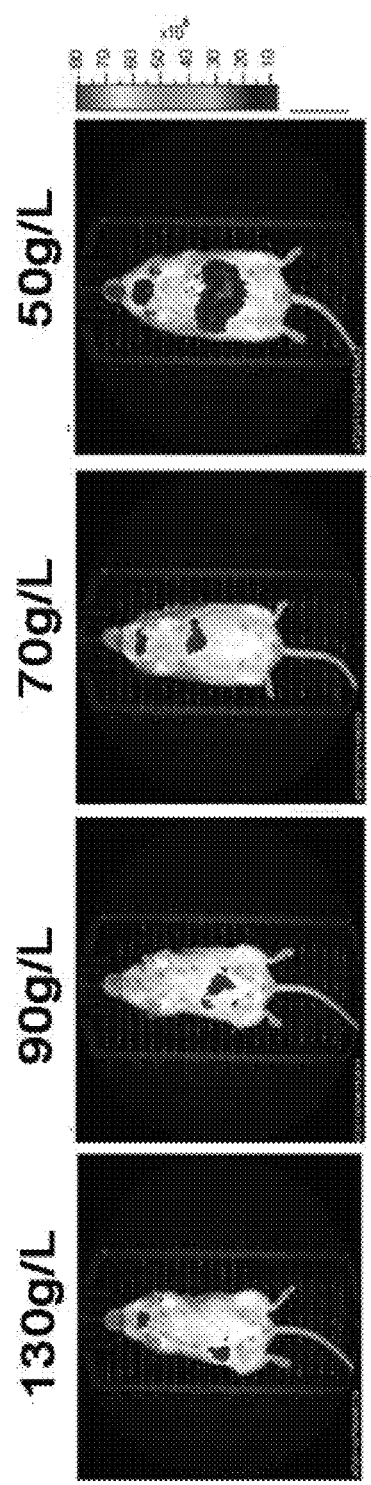
Figure 8C:
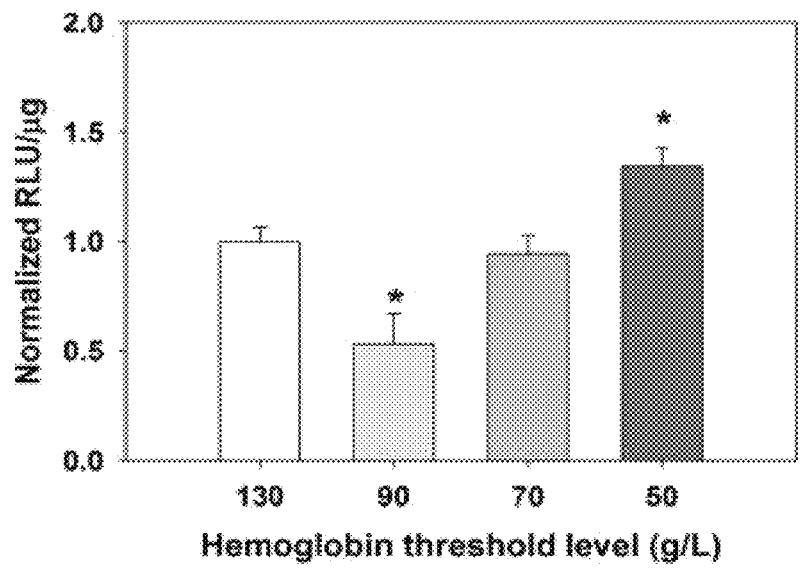
Figure 8D:
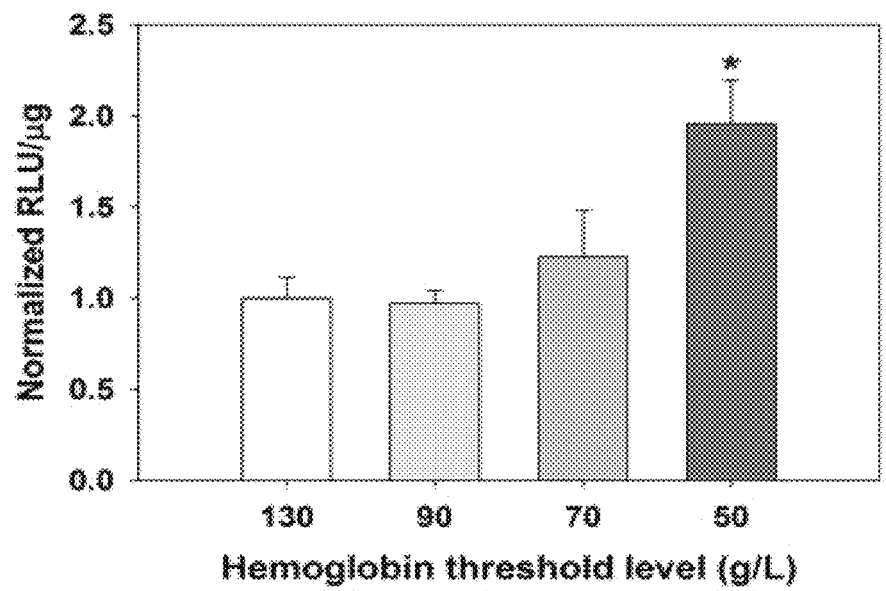
Figure 8E:
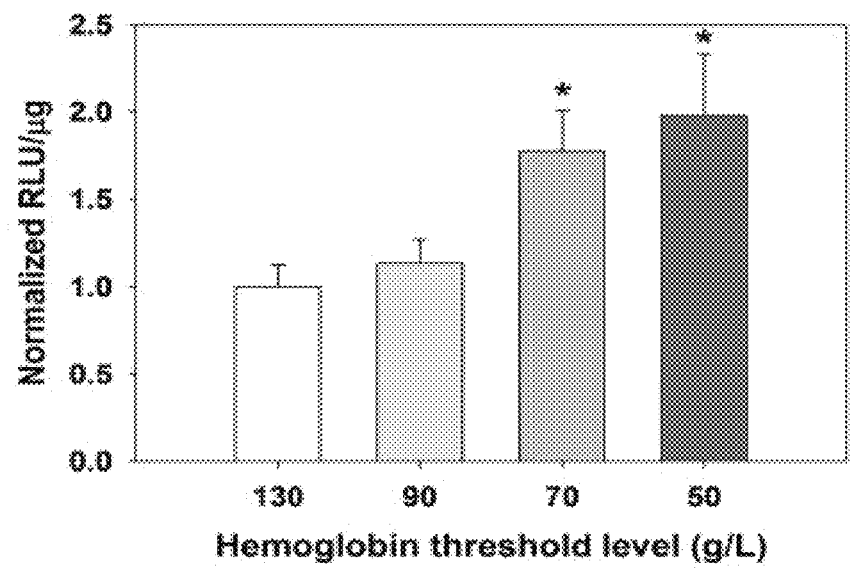
Figure 8F:
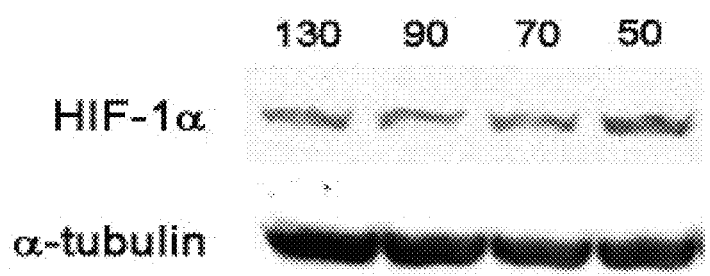
Figure 8G:
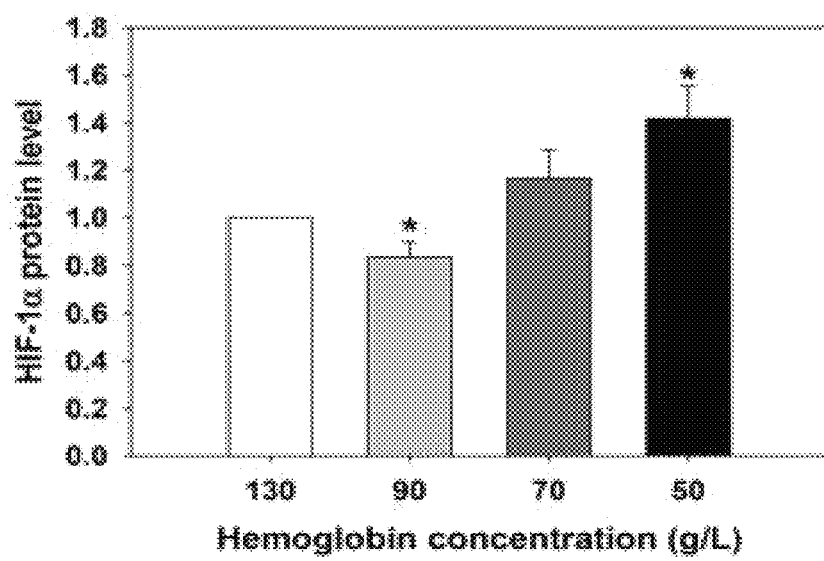
Figure 8H:
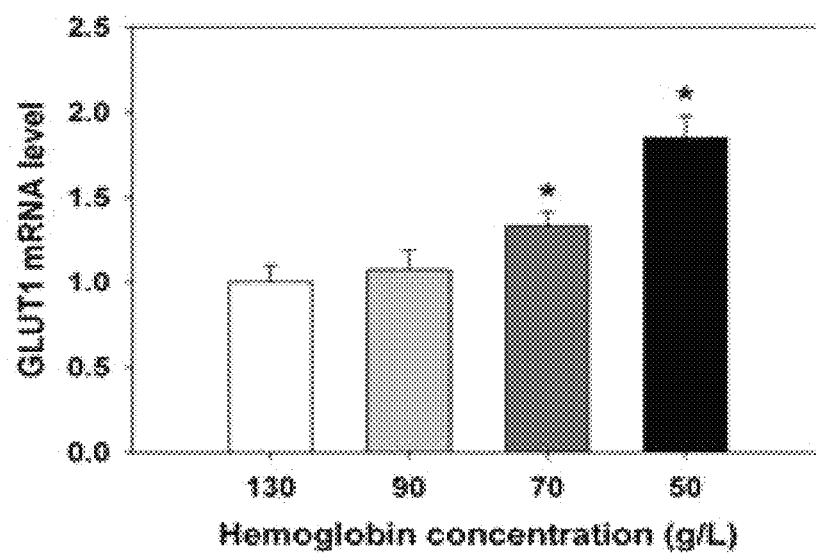
Figure 8I:
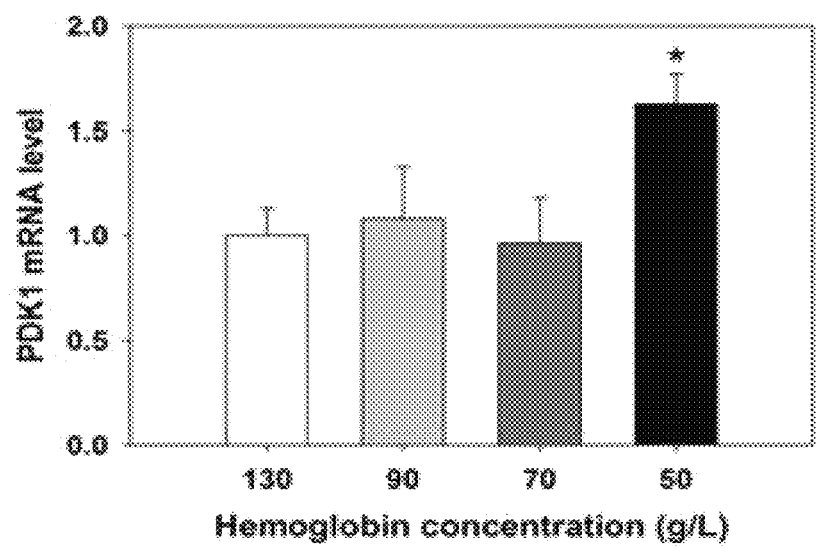
Figure 8J:
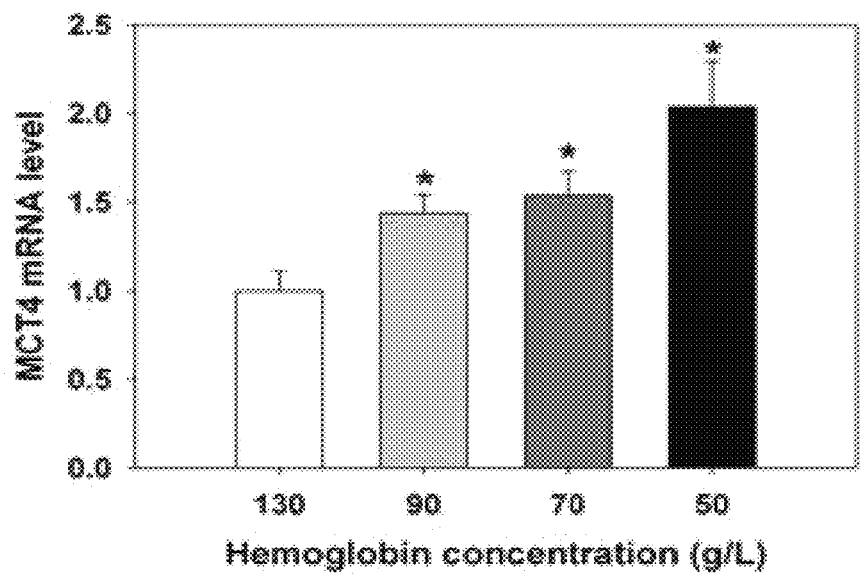
Figure 8K:
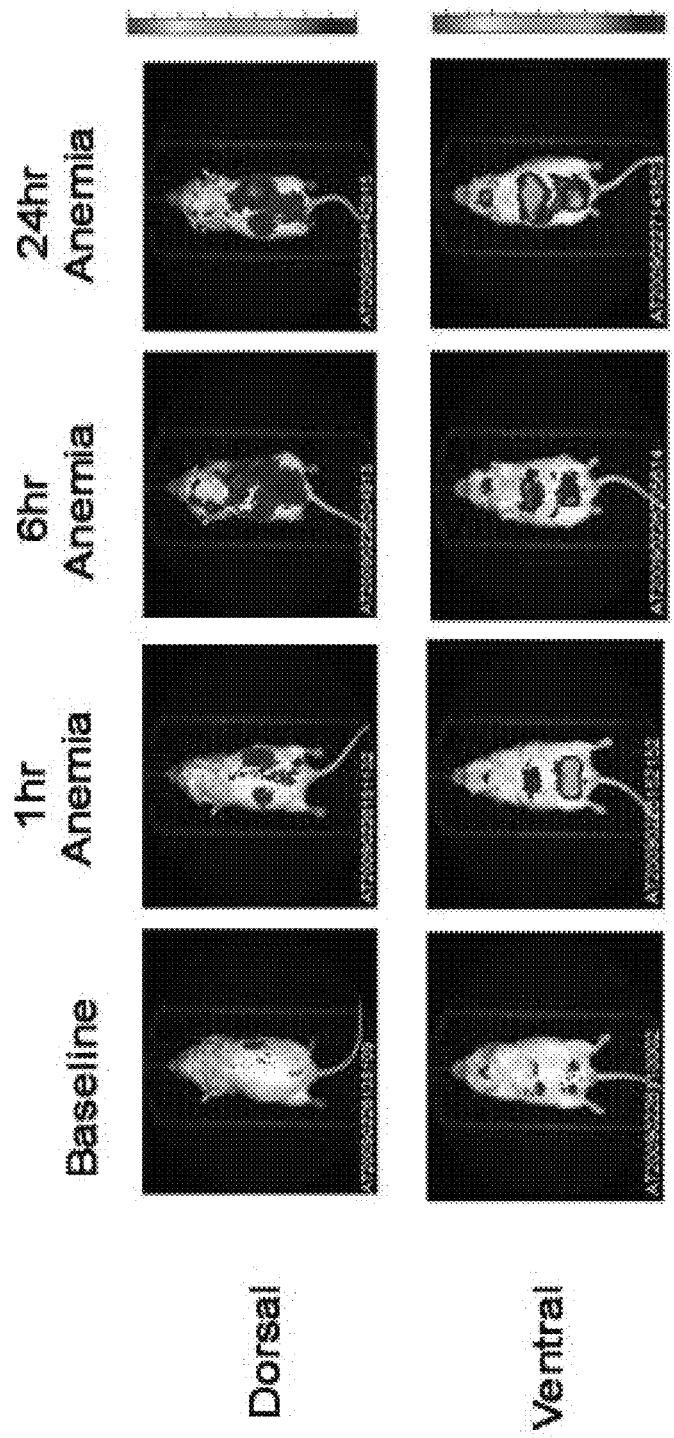
Figure 8L:
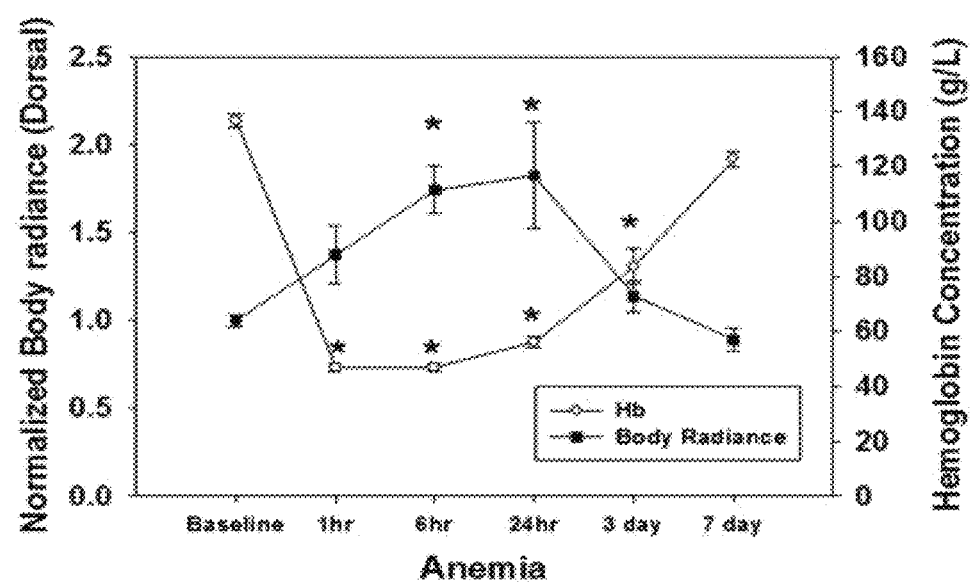

FIG. 7 is a bar graph depicting NO sequestration rate for four nanoparticle formulations (F-1, F-2, F-3, and F-4; see Table 2) in comparison to physiological controls (RBCs and cell-free Hb). The initial rate of NO scavenging was calculated by fitting a tread line to the first ~1 min of data following sample injection. * p<0.05; one way ANOVA (n=5). Cell-free Hb sequesters NO more avidly than do intact RBCs (as is known); all nanoparticle formulations sequester NO less avidly than RBCs, with the exception of F-3 (equivalent to RBCs).

FIG. 8A-L depicts graphs and images showing whole body and tissue HIF levels vary as a function of [Hb] in HIF-α (ODD)-luciferase mice. (A-B) Whole body HIF-luciferase level was significantly increased during hemodilutional anemia. In (A) depicts HIF-luciferase levels graphically, and (B) depicts images of the whole animal. (C-E) Tissue-specific HIF-luciferase luminescence changes in a similar fashion; brain (C), kidney (D) and liver (E). (F-G) Similar to (C-E), measurement of brain HIF-1 α protein expression by western blot increased proportionally with hemodilution. (F) depicts an image of a western blot of HIF-α and a control (α-tubulin); in (G), the levels of HIF-α protein are graphically depicted. (H-J) Likewise, selected HIF-dependent mRNA levels increase as well: (H) GLUT1, (I) PDK1, (J) MCT4. (K-L) Depicts images and graphs showing the relationship of Hb levels and whole body HIF luciferase. Specifically, HIF luciferase signal is inversely related to Hb during both development of, and resolution from, anemia. (K) whole body imaging and (L) normalized body radiance (left y-axis) or hemoglobin concentration (right y-axis) vs. anemia (x-axis). NB: Paired measurements of brain $pO_2$ during acute hemodilution (by phosphorescence quenching) correlate with [Hb], affirming analysis HIF expression trends. For the following measurements of ([Hb] (g/L) & $pO_2$ (mmHg), (mean±SD)), N=8 mice: Hb of 125.1±8.3→$pO_2$ of 65.0±8.3; Hb of 88.3±5.4→$pO_2$ of 56.4±9.5; Hb of 72.5±7.4→$pO_2$ of 52.1±10.3; Hb of 52.4±3.9→$pO_2$ of 40.6±6.8.

Figure 9A:
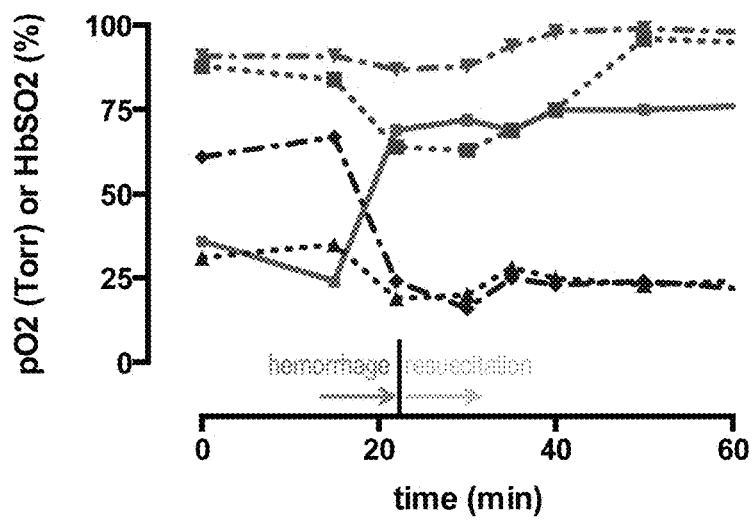
Figure 9B:
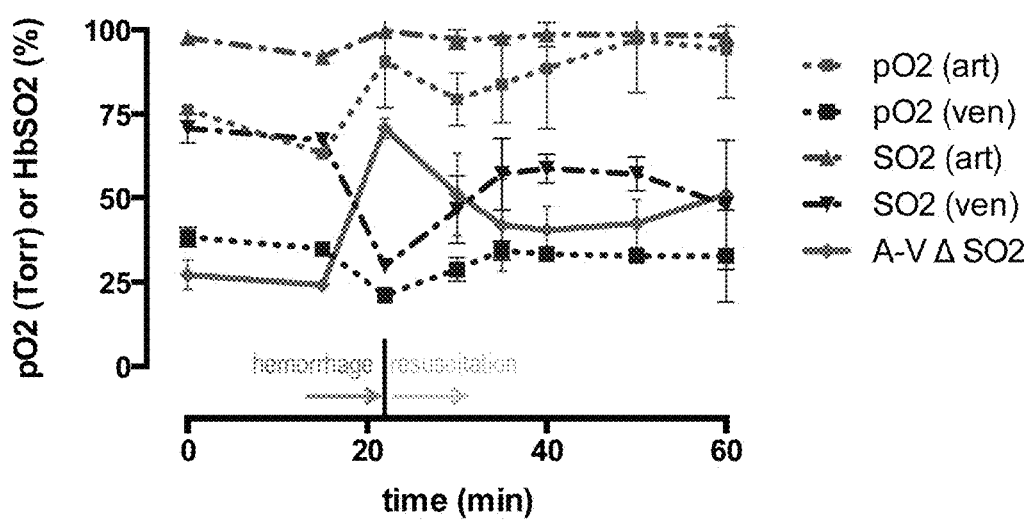
Figure 9C:
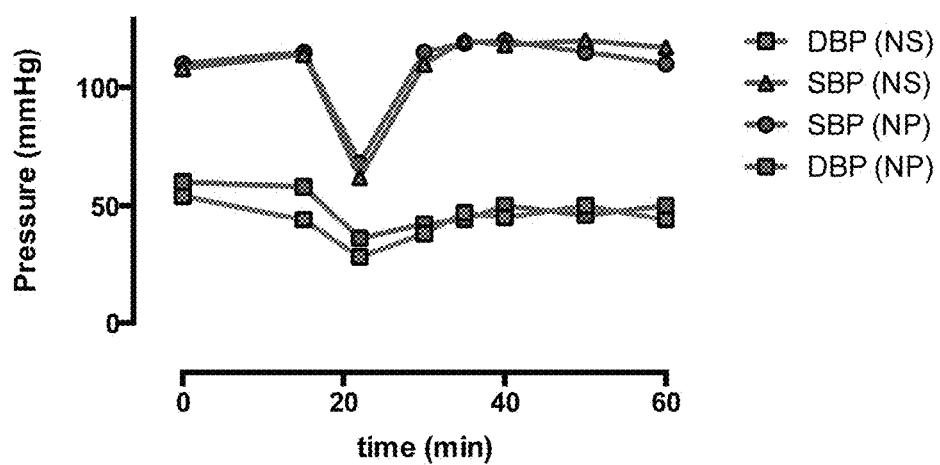

FIG. 9A-C depicts graphs showing the efficacy of a nanoparticle in a rodent hemorrhagic shock model. The graphs in (A) and (B) illustrates an expected, striking increase in the AV $O_2$ difference with blood removal (rising from 24 to 67%), that (A) persisted following resuscitation with normal saline and (B) resolved following resuscitation with the blood substitute (normalizing from 67 to 31%). (C) A difference was not observed in the hemodynamic effect afforded by either resuscitation fluid (Normal Saline=NS, Nanoparticle Solution=NP), suggesting that the benefit in $O_2$ delivery from the blood substitute arises from improved $O_2$ content, in addition to restoration of blood pressure.

DETAILED DESCRIPTION

The present disclosure provides oxygen-carrying nanoparticles that are morphologically similar to red blood cells. Oxygen-carrying nanoparticles of the disclosure are self-assembled, which means they are relatively quick and easy to prepare. Oxygen-carrying nanoparticles of the disclosure are also substantially bi-concaved disc shaped providing increased mechanical stability. Oxygen-carrying nanoparticles of the disclosure comprise a payload. The payload comprises an oxygen-carrying agent, an allosteric effector and a reducing agent. Advantageously, an oxygen-carrying nanoparticle of the disclosure is capable of incorporating high per particle payload, and is capable of mimicking the oxygen-carrying characteristics of red blood cells by shifting the affinity of the oxygen-carrying agent to oxygen based on tissue need. In addition, an oxygen-carrying nanoparticle does not alter vascular tone, is capable of maintaining oxygen-carrying functionality during circulation, and avoids tissue extravasation through reticuloendothelial-based particle clearance. Importantly, nanoparticles of the disclosure may be lyophilized for extended storage, and may be rapidly reconstituted before use.

Solutions comprising nanoparticles and methods of using the nanoparticles and solutions are also described.

I. Nanoparticle

One aspect of the disclosure provides a substantially bi-concaved disc shaped oxygen-carrying nanoparticle. The nanoparticle comprises an aqueous core, a shell comprising an amphiphilic polymer, and a payload. The payload comprises an oxygen-carrying agent, an allosteric effector, and a reducing agent. Each aspect of a nanoparticle is described in detail below. Nanoparticles may also be as described in U.S. Patent Application No. 2010/0297007, the disclosure of which is incorporated herein by reference in its entirety.

(a) Morphology

A nanoparticle comprises a toroidal, i.e., substantially bi-concaved disc shape. Such nanoparticles have a generally rounded, plate-like form of finite thickness which is concave on both surfaces, mimicking the shape of a human red blood cell, and increasing the surface area of a nanoparticle when compared to a spherical nanoparticle, therefore enhancing oxygen exchange dynamics of an oxygen-carrying nanoparticle. The concavity of the nanoparticles may take the form of a concave depression on each surface, or an opening, or "through-hole" through the approximate center of the disc. Within a population of nanoparticles, some of the nanoparticles may comprise a depression, and some of the nanoparticles may comprise a through-hole. In general, at least about 50% of a population of nanoparticles may be bi-concaved disc shaped. The percentage of bi-concaved disc shaped nanoparticles may be about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%' 88%, 89%, 90%, 91%, 92%, 93%, 94%, 95%, 96%, 97%, 98% or 99% of the total population of nanoparticles. Alternatively, the percentage of bi-concaved disc shaped nanoparticles may be at least about 50%, 55%, 60%, 65%, 70%, 75%, 80%, 85%, 90%, 95%, 97%, 98%, or 99% A of the total population of nanoparticles.

Because of the shape of nanoparticles, the diameter of a nanoparticle is greater than the height of the nanoparticle. In general, the diameter of a nanoparticle may range from about 50 nanometers to about 500 nanometers, and the height of a nanoparticle may range from about 20 nanometers to about 150 nanometers. As such, the diameter of a nanoparticle may range from about 100 nanometers to about 300 nanometers, and the height of a nanoparticle may range from about 40 nanometers to about 85 nanometers. Alternatively, the diameter of a nanoparticle may range from about 100 nanometers to about 250 nanometers, and the height of a nanoparticle may range from about 30 nanometers to about 80 nanometers. Preferably, the diameter of a nanoparticle may range from about 120 nanometers to about 250 nanometers, and the height of a nanoparticle may range from about 50 nanometers to about 70 nanometers. The diameter of a nanoparticle may also be about 100, 110, 120, 130, 140, 150, 160, 170, 180, 190, 200, 210, 220, 230, 240, 250, 260, 270, 280, 290, or 300 nanometers, and the height of a nanoparticle may be about 40, 45, 50, 55, 60, 65, 70, 75, 80, or 85 nanometers.

Nanoparticles comprising a population of nanoparticles are substantially uniform in size, wherein size is measured as the diameter of a nanoparticle. The variation in size among nanoparticles of the population is less than about 15%. Preferably, the variation in size among nanoparticles of the population may be less than about 10%, and even more preferably less than about 5%. The variation in size among nanoparticles of the population may be less than about 10%, 9%, 8%, 7%, 6%, 5%, 4%, 3%, 2%, or 1%.

The size between two or more populations of nanoparticles can and will vary, wherein size is measured as the diameter of a nanoparticle. Size of a nanoparticle may be influenced by the types and concentrations of oxygen-carrying agent, allosteric effector, reducing agent, and amphiphilic polymer and/or optional agents. While not wishing to be bound by theory, it is believed the size of a nanoparticle may increase with increasing concentrations of oxygen-carrying agent, allosteric effector, reducing agent and/or optional agents. The size of a nanoparticle may also increase with as the molecular weight of the branched polymer comprising the amphiphilic polymer increases.

In general, bi-concaved disc shaped nanoparticles have increased stability relative to non-bi-concaved disc shaped nanoparticles. Stability may be measured by changes in the particle diameter, zeta potential and/or polydispersity over time. Stability may also be measured by changes in the release of the payload over time (e.g. release of an oxygen-carrying agent, allosteric effector and/or reducing agent over time). A stable nanoparticle may reflect less than about 20%, preferably less than about 15%, more preferably less than about 10% change from baseline properties. Bi-concaved disc shaped nanoparticles are stable at room temperature for at least several months, for more than two months, or for more than three months. Stability is typically measured for a population of nanoparticles rather than a single nanoparticle. In general, bi-concaved disc shaped nanoparticles are stable at 4° C. for at least several months, or for more than two months. Further details are provided in the Examples.

(b) Shell

A shell of a bi-concaved disc shaped nanoparticle comprises an amphiphilic polymer, wherein the amphiphilic polymer comprises a branched polymer covalently conjugated to lipids. The shell may also comprise water, a buffer solution, a saline solution, a serum solution, and combinations thereof. The shell may further comprise a biologically active agent, an imaging agent, a metal atom, or a therapeutic agent, as detailed below.

A shell of a bi-concaved disc shaped nanoparticle is bi-layered, comprised of a hydrophilic outer layer, a hydrophilic inner layer, and a hydrophobic region between the layers. To form the shell of a nanoparticle, an amphiphilic polymer first self-assembles to form a bi-layer comprised of a hydrophilic outer layer, a hydrophilic inner layer, and a hydrophobic region between the layers, and then self-assembles into a bi-concaved disc shaped nanoparticle. The formation of the bi-concaved disc shaped particle is driven by the hydrophobic-hydrophilic block ratio of the amphiphilic polymer and the self-assembly procedure of the nanoparticles.

The amphiphilic polymer may comprise from about 1% to about 40% by weight of the nanoparticle. For example, the amphiphilic polymer may comprise about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, or about 40% by weight of the nanoparticle. The amphiphilic polymer may comprise from about 1% to about 15%, about 5% to about 20%, about 1% to about 10%, or about 10% to about 20% by weight of the nanoparticle. Alternatively, the amphiphilic polymer may comprise from about 1% to about 5%, about 5% to about 10%, about 10% to about 15%, or about 15% to about 20% by weight of the nanoparticle.

Additional aspects are described in detail below.

i. Branched Polymers

A branched polymer may be a branched, amine-containing polymer with one or more free reactive group. Non-limiting types of suitable branched polymers include star branched polymers, graft branched polymers, comb branched polymers, brush branched polymers, network branched polymers, hyperbranched polymers, and dendritic polymers.

The polymer may be a synthetic polymer, a semi-synthetic polymer, or a natural polymer. Non-limiting examples of suitable polymers include polyacrylate, polyacrylamide, polyacrylamide sulphonic acid, polyacrylonitrile, polyamines, polyamides, polyamidoamine (PAMAM), polybutadiene, polydimethylsiloxane, polyester, polyether, polyethylene, polyethylene glycol (PEG), polyethyleneimine (PEI), polyethyleneoxide, polyethyleneglycol, polyethyloxazoline, polyhydroxyethylacrylate, polyisoprene, polymethacrylate, polymethacrylamide, polymethylmethacrylate, polymethyloxazoline, polyoxyalkylene oxide, polyphenylene, polypropyleneimine, polypropylene oxide, polystyrene, polyurethane, polyvinyl alcohol, polyvinylpyrrolidone, methylcellulose, carboxymethylcellulose, hydroxyethylcellulose, hydroxypropylcellulose, hydroxypropylmethylcellulose, hyaluronic acid, dextran, dextrin, heparan sulfate, chondroitin sulfate, heparin, alginate, agar, carrageenan, xanthan, guar, polyamino acids (such as e.g., polylysine, polyglycine, and polyserine), co-polymers, and combinations thereof.

A branched polymer comprises at least one type of reactive group. Suitable reactive groups include, but are not limited to, primary, secondary or tertiary amines, carboxylate, hydroxyl, alkyl, fluoroalkyl, aryl, acetate, amide, ester, sulfone, sulfoxide, sulfonate, sulfonamide, phosphonate, and phosphonamide groups.

The average molecular weight of a branched polymer can and will vary. For example, polymers of an increasing molecular weight may be selected to produce an outer shell of an increasing thickness. The molecular weight may be expressed as the number average molecule weight ($M_n$) or the weight average molecule weight ($M_w$). In general, the number and weight average molecular weight of a branched polymer may range from about 200 to about 1,000,000 Daltons. The number and weight average molecular weight of a branched polymer may range from about 200 to about 50,000 Daltons, including from about 200 to about 5,000, from about 5,000 to about 50,000, from about 50,000 to about 250,000, or from about 250,000 to about 1,000,000 Daltons. Preferably, the number and weight average molecular weight of a branched polymer may be about 10,000 Daltons, about 25,000 Daltons, or about 50,000 Daltons.

While not wishing to be bound by theory, it is believed the inherent nature of a branched polymer enables retention of an allosteric effector (described in Section I(f)) via electrostatic interaction. One skilled in the art will appreciate that the choice of branched polymer may influence this interaction. For example, when a branched polymer is a cationic branched polymer with secondary or tertiary amines, the amine density may be an important factor. It is not necessary, however, for a branched cationic polymer to be a cationic branched polymer to electrostatically interact with an allosteric effector. For making an electrostatic interaction with an allosteric effector, the amines of a branched polymer are sufficient. Preferred branched polymers may include, but are not limited to, a polyethyleneimine branched polymer, a PAMAM dendrimer, a star polymer, or a graft polymer. Even more preferably, the branched polymer is a polyethyleneimine branched polymer. An exemplary branched polymer is a 10K polyethyleneimine branched polymer, a 50K polyethyleneimine branched polymer, or a 100K polyethyleneimine branched polymer. An exemplary branched polymer is G4 polyamidoamine.

ii. Lipids

An amphiphilic polymer also comprises lipids linked to a branched polymer. A lipid may be covalently linked or non-covalently linked to a branched polymer. While not wishing to be bound by theory, it is believed the percentage of reactive groups of a branched polymer linked to lipids influences the hydrophobic character, and thus morphology, of the particle. The percentage of free reactive groups of a branched polymer linked to a lipid will vary with the materials in order to control the hydrophobic-hydrophilic block ratio, which drives the formation of bilayer-type membranes into biconcave disc-like shaped particles. Generally, an amphiphilic polymer comprises lipids linked to a branched polymer, wherein at least about 25% of reactive groups of a branched polymer are linked to lipids. For example, the percentage of free reactive groups linked to lipids may be 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The percentage of reactive groups linked to lipids may also be at least about 25%, 30%, 35%, 40%, 45%, 50%, 55%, 60%, 65%, 70%, or 75%, or greater than 75%. Preferably, the percentage of free reactive groups linked to lipids may range from about 40% to about 70% or from about 50% to about 60%. An exemplary percentage of free reactive groups linked to lipids may be about 55%.

Non-limiting examples of suitable lipids include fatty acids, fatty acid esters, phospholipids, bile acids, glycolipids, aliphatic hydrophobic compounds, and aromatic hydrophobic compounds. A lipid may be natural, synthetic, or semi-synthetic. In general, a lipid comprises a polar head group and at least one hydrophobic hydrocarbyl or substituted hydrocarbyl group. A polar head group links a lipid to a branched polymer via a covalent bond. Examples of suitable polar head groups include, but are not limited to, carboxy, acyl, propargyl, azide, aldehyde, thiol, ester, sulfate, and phosphate. Preferred hydrophobic hydrocarbyl groups include, but are not limited to, alkyl, alkynyl, heterocylic, and combinations thereof. Typically, alkyl or alkynyl groups comprise from about six to about 30 carbon atoms, or more preferably from about 12 to about 24 carbon atoms. A substituted hydrocarbyl group refers to hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbamate, carbocyclo, cyano, ester, ether, halogen, heterocyclo, hydroxyl, keto, ketal, phospho, nitro, thio, trifluoromethyl, sulfonyl, sulfonamide, and the like. A lipid may be a phospholipid such as, e.g., phosphatidyl ethanolamine, phosphatidyl serine, phosphatidyl inositol, cardiolipin, phosphatidyl ethylene glycol, and the like, or a bile acid such as cholic acid. Preferably, a lipid may be a fatty acid, wherein the fatty acid chain comprises an alkyl (saturated) or an alkynyl (unsaturated) group as defined above. Preferred fatty acids include, but are not limited to, 10,12-pentacosadiynoic acid, hexadecyloctadecanoic acid, cholanic acid, linoleic acid, C24-pentacosadiynoic acid, and palmitic acid. Preferably, a lipid may be palmitic acid or C24-pentacosadiynoic acid.

An exemplary branched polymer may be polyethyleneimine and an exemplary lipid is palmitic acid, C24-pentacosadiynoic acid, or linoleic acid, wherein at least about 40% of the free reactive groups of the polymer are linked to the lipid. An exemplary branched polymer may be polyethyleneimine and an exemplary lipid is palmitic acid, C24-pentacosadiynoic acid, or linoleic acid, wherein at least about 50% of the free reactive groups of the polymer are linked to the lipid. An exemplary branched polymer may be polyethyleneimine and an exemplary lipid is palmitic acid, C24-pentacosadiynoic acid, or linoleic acid, wherein at least about 55% of the free reactive groups of the polymer are linked to the lipid. When the branched polymer is polyethyleneimine, the free reactive group is an amine, typically a primary amine and/or a secondary amine.

An exemplary branched polymer may be PAMAM and an exemplary lipid is palmitic acid, C24-pentacosadiynoic acid, or linoleic acid, wherein at least about 10% of the free reactive groups of the polymer are linked to the lipid. An exemplary branched polymer may be PAMAM and an exemplary lipid is palmitic acid, C24-pentacosadiynoic acid, or linoleic acid, wherein at least about 20% of the free reactive groups of the polymer are linked to the lipid. An exemplary branched polymer may be PAMAM and an exemplary lipid is palmitic acid, C24-pentacosadiynoic acid, or linoleic acid, wherein at least about 30% of the free reactive groups of the polymer are linked to the lipid. When the branched polymer is PAMAM, the free reactive group is an amine, typically a primary amine.

(c) Aqueous Core

Nanoparticles comprise an aqueous core. The aqueous core may comprise water, a buffer solution, a saline solution, a serum solution, and combinations thereof. The aqueous core may also comprise a biologically active agent, an imaging agent, a metal atom, a therapeutic agent, an oxygen-carrying agent, an allosteric effector, a reducing agent, or combinations thereof, as detailed below. Preferably, the aqueous core comprises an oxygen-carrying agent, an allosteric effector, and a reducing agent.

(d) Intra-Molecular Cross-Linking of the Particle Exterior

The exterior of the nanoparticle comprises the outer layer of the shell. The outer layer of the shell is intra-molecularly cross-linked in order to neutralize the surface reactive groups. Stated another way, the outer layer of the shell is intra-molecularly cross-linked such that the nanoparticle has a near neutral surface. The degree of cross-linking needed to achieve a near neutral surface will vary depending upon the amphiphilic polymer. Nanoparticles with a zeta potential of about −15 to about +15 mV are considered approximately neutral. A nanoparticle with a near neutral surface may have a zeta potential between −15, −14, −13, −12, −11, −10, −9, −7, −6, −5, −4, −3, −2, −1, 0, +1, +2, +3, +4, +5, +6, +7, +8, +9, +10, +11, +12, +13, +14, or +15 mV. A nanoparticle with a near neutral surface may also have a zeta potential of about −15 to about 0 mV, about −10 to about 0 mV, about −10 to about −5 mV, about −9 to about −4 mV, about −8 to about −3 mV, about −7 to about −2 mV, about −6 to about −1 mV, or about −5 to about 0 mV. Alternatively, a nanoparticle with a near neutral surface may also have a zeta potential of about 0 to about +15 mV, about 0 to about +10 mV, about +5 to about +10 mV, about +4 to about +9 mV, about +3 to about +8 mV, about +2 to about +7 mV, about +1 to about +6 mV, or about 0 to about +5 mV. Zeta potential can affect a nanoparticle's tendency to interact with proteins, microparticles, cells and other biomolecules. A near neutral surface is an important feature of a nanoparticle of the disclosure, since the nanoparticles will be administered to a subject and it is undesirable for the nanoparticle to substantially interact with proteins, cells and other particles in the blood. Without wishing to be bound by theory, Applicants also believe the degree of cross-linking substantially contains the payload within the interior of the particle, affects the diffusion of gases such as oxygen, carbon dioxide and nitric oxide into or within the nanoparticle. Cross-linking may also impart increased mechanical stability to nanoparticles, improve biocompatibility and/or extend circulation longevity. Cross-linking may also inhibit oxidative damage to an oxygen-carrying agent.

Surface lipids of the amphiphilic polymer of the outer shell may be cross-linked by chemical means. Alternatively, a core polymer of the amphiphilic polymer may be cross-linked by photo-chemical means. Generally, at least about 30% of the available reactive groups of an amphiphilic polymer may be cross-linked, more than 30%, 40%, 50%, 60%, 70%, 80%, 90%, or 95% A of the available reactive groups of the amphiphilic polymer may be cross-linked. Suitable means of cross-linking are detailed below in Section II. The degree of cross-linking may be determined by any method known in the art.

Preferably, the particle surface is intramolecularly cross-linked with a bifunctional linker, such that at least about 30% of the surface reactive groups of the amphiphilic polymer may be cross-linked, including about 30% to about 50%, about 50% to about 70%, or about 70% to about 100%. Preferred bifunctional linkers include, but are not limited to, activated (or functionalized) short PEG chains. Alternatively, coupling agents may be used. Short PEG chains may comprise about 1, 2, 3, 4, 5, or about 6 ethylene oxide monomers. Preferably, short PEG chains comprise 1 to 3 ethylene oxide monomers, or more preferably, 2 ethylene oxide monomers. Exemplary bifunctional linkers may include ethylene glycol bis(sulfosuccinimidylsuccinate) (Sulfo-EGS), epoxides, tosylates or chloroformates. Further details are provided below in Section II.

(e) Optional PEGylation

Additionally, an amphiphilic polymer of a nanoparticle may be derivatized with polyethylene glycol (PEG), as detailed below in Section II. Preferably, a nanoparticle is derivatized using short PEG chains. Short PEG chains may comprise about 1, 2, 3, 4, 5, or about 6 ethylene oxide monomers. Preferably, short PEG chains comprise 1 to 3 ethylene oxide monomers, or more preferably, 2 ethylene oxide monomers.

(f) Payload

A nanoparticle of the disclosure comprises a payload, the payload comprising an oxygen-carrying agent, an allosteric effector, and a reducing agent. The payload is contained in the interior of the nanoparticle. An oxygen-carrying agent, an allosteric effector, and a reducing agent of an oxygen-carrying nanoparticle may be contained within the aqueous core of the nanoparticle, may be within the hydrophilic region of the inner layer comprising the shell of the nanoparticle, may be within the hydrophobic region comprising the shell of the nanoparticle, or a combination thereof. It is also envisioned that an oxygen-carrying agent, an allosteric effector, and a reducing agent may be localized to different locations of a nanoparticle.

i. Oxygen-Carrying Agent

A nanoparticle of the disclosure comprises an oxygen-carrying agent. Any molecule capable of carrying oxygen may be suitable for use as an oxygen-carrying agent. Non limiting examples of oxygen-carrying agents include perfluorocarbon-based oxygen carriers (PFBOC), hemoglobin-based oxygen carriers (HBOC), hemoglobin-like oxygen carriers such as leghemoglobin, and artificial hemoglobin-based oxygen carriers such as hemin. As such, an oxygen-carrying agent may be a hemoglobin-based oxygen carrier (HBOC), a hemoglobin-like oxygen carrier, a PFBOC, or an artificial hemoglobin-based oxygen carrier.

Nanoparticles may comprise about 2000 to about 10,000 oxygen-carrying agent molecules per nanoparticle. Nanoparticles may comprise about 2000, 2500, 3000, 3500, 4000, 4500, 5000, 5500, 6000, 6500, 7000, 7500, 8000, 8500, 9000, 9500, or about 10,000 oxygen-carrying agent molecules per nanoparticle. Nanoparticles may also comprise more than about 10,000 oxygen-carrying agent molecules per nanoparticle. The absolute number of oxygen-carrying agent molecules per nanoparticle can and will vary depending on the size of the nanoparticle, affinity of the oxygen-carrying agent for oxygen, and ability to limit auto-oxidation formation during $O_2$ offloading.

About 20% to about 60% (w/v) of a nanoparticle of the disclosure may comprise an oxygen-carrying agent. For example, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (w/v) of a nanoparticle may comprise an oxygen-carrying agent. Alternatively, about 20%, 25%, 30%, 35%, 40%, 45%, 50%, 55%, or about 60% (w/v) of a nanoparticle comprises an oxygen-carrying agent. Preferably, about 25% to about 60%, about 30% to about 60%, about 35% to about 60%, about 40% to about 60%, about 45% to about 60%, about 50% to about 60% (w/v) of a nanoparticle comprises an oxygen-carrying agent.

Preferably, an oxygen-carrying agent is an artificial hemoglobin-based oxygen carrier such as hemin. Even more preferably, an oxygen-carrying agent is a hemoglobin-based oxygen carrier. Hemoglobin is an iron-containing oxygen transport metalloprotein, and is the main component of red blood cells, comprising about 33% of the cell mass. Each molecule of hemoglobin has 4 subunits, two α chains and two β chains, which are arranged in a tetrameric structure. Each subunit also contains one heme group, which is the iron-containing center that binds oxygen. As such, each hemoglobin molecule can bind four oxygen molecules.

The present disclosure is not limited by the source of hemoglobin. The term "hemoglobin" refers to naturally occurring or synthetic hemoglobin. For example, a hemoglobin-based oxygen-carrying agent of the disclosure may be from animals. Alternatively, a hemoglobin-based oxygen-carrying agent of the disclosure may be from humans. Preferred sources of hemoglobin are humans, cows and pigs.

A hemoglobin oxygen-based carrying agent may be isolated and purified from a human or animals such as cows and pigs. Alternatively, a hemoglobin-based oxygen-carrying agent may be produced by chemical synthesis and recombinant techniques. Human α- and β-globin genes have both been cloned and sequenced (See for example, Liebhaber et al., P.N.A.S. 77: 7054-7058 (1980); Marotta et al., J. Biol. Chem. 353: 5040-5053 (1977) (beta-globin cDNA).

It will be appreciated by those skilled in the art that hemoglobin amino acid sequence polymorphisms may exist within a population (e.g., the human, cow or pig population). Such genetic polymorphism may exist among individuals within a population due to natural allelic variation. Any and all such amino acid variations and resulting polymorphisms that are the result of natural allelic variation and that do not alter the functional activity of hemoglobin are intended to be within the scope of the disclosure. Similarly, the term hemoglobin oxygen-based carrying agent includes hemoglobin that have been engineered to adjust the oxygen binding and release properties of hemoglobin when used as an oxygen-carrying agent in an oxygen-carrying nanoparticle (See, e.g., Nagai, et al., (1985) P.N.A.S., 82: 7252-7255, and U.S. Pat. No. 5,028,588). A hemoglobin oxygen-based carrying agent may also be naturally occurring hemoglobin, chimeric hemoglobin, recombinant hemoglobin, hemoglobin fragments, or hemoglobin comprising combinations thereof without departing from the scope of the disclosure.

A hemoglobin oxygen-based carrying agent may be either native or subsequently modified by a chemical reaction such as intra- or inter-molecular cross-linking, polymerization, or the addition of chemical groups such as polyalkylene oxides or other adducts. Representative examples of modified hemoglobin oxygen-carrying agents are disclosed in a number of issued United States Patents, including U.S. Pat. No. 4,857,636, U.S. Pat. No. 4,600,531, U.S. Pat. No. 4,061,736, U.S. Pat. No. 3,925,344, U.S. Pat. No. 4,529,719, U.S. Pat. No. 4,473,496, U.S. Pat. No. 4,584,130, U.S. Pat. No. 5,250,665, U.S. Pat. No. 4,826,811, and U.S. Pat. No. 5,194,590.

Preferably, an oxygen-carrying agent is hemoglobin isolated from humans, cows, or pigs. Even more preferably, an oxygen-carrying agent is hemoglobin isolated from humans. Methods of isolating hemoglobin from a subject are known in the art and may be as described in the examples and in Rogers et al., 2009, FASEB Journal 23:3159-3170, the disclosure of which is incorporated herein in its entirety. Alternative methods for isolating hemoglobin are also known in the art. For example, hemoglobin may be purified from a donor using tangential flow filtration. See, for example, Elmer et al., 2011, Journal of chromatography B, Analytical technologies in the biomedical and life sciences, 879:1311-138, and/or Palmer et al., 2009, *Biotechnol. Prog.*, 25:189-199. Irrespective of the source of hemoglobin, a hemoglobin oxygen-carrying agent is substantially pure, and free of stroma and endotoxin.

Nanoparticles may comprise about 2000 to about 10,000 hemoglobin molecules per nanoparticle. Nanoparticles may comprise about 2000, 2500, 3000, 3500, 4000, 4500, 5000, 5500, 6000, 6500, 7000, 7500, 8000, 8500, 9000, 9500, or about 10,000 hemoglobin molecules per nanoparticle or more. A nanoparticle may comprise about 2000 to about 6000 hemoglobin molecules per nanoparticle or about 6000 to about 10000 hemoglobin molecules per nanoparticle. A nanoparticle may also comprise about 3000 to about 6000 hemoglobin molecules per nanoparticle, about 4000 to about 7000 hemoglobin molecules per nanoparticle, about 5000 to about 8000 hemoglobin molecules per nanoparticle, about 6000 to about 9000 hemoglobin molecules per nanoparticle, or about 7000 to about 10,000 hemoglobin molecules per nanoparticle. Alternatively, a nanoparticle may comprise about 3000 to about 4000 hemoglobin molecules per nanoparticle, about 4000 to about 5000 hemoglobin molecules per nanoparticle, about 5000 to about 6000 hemoglobin molecules per nanoparticle, about 6000 to about 7000 hemoglobin molecules per nanoparticle, about 7000 to about 8000 hemoglobin molecules per nanoparticle, about 8000 to about 9000 hemoglobin molecules per nanoparticle, or about 9000 to about 10,000 hemoglobin molecules per nanoparticle. The absolute number of hemoglobin molecules per nanoparticle can and will vary depending on the size of the nanoparticle.

Generally, about 20% to about 60% (w/v) of a nanoparticle may comprise hemoglobin. For example, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% (w/v) of a nanoparticle may comprise hemoglobin. Alternatively, about 20%, 25%, 30%, 35%, 40%, 45%, 50%, 55%, or about 60% (w/v) of a nanoparticle comprises hemoglobin. Preferably, about 25% to about 60%, about 30% to about 60%, about 35% to about 60%, about 40% to about 60%, about 45% to about 60%, about 50% to about 60% (w/v) of a nanoparticle comprises hemoglobin. While not wishing to be bound by theory, it is believed that the high concentration of hemoglobin may stabilize hemoglobin, and prevent concentration-dependent hemoglobin tetramer dissociation into individual α and β dimmers.

If the hemoglobin concentration of an oxygen-carrying nanoparticle cannot be determined directly, as described herein, it may be estimated from the iron content of the nanoparticle. The iron content of hemoglobin is known in the art. See, for example, Bernhart F W and Skeggs L 1943 *J Biol Chem* 147:19-22.

ii. Allosteric Effector

A nanoparticle of the disclosure comprises an allosteric effector that modulates the affinity of an oxygen-carrying agent to oxygen, and modulates the rate or amount of oxygen binding to, or releasing from, an oxygen-carrying agent in a nanoparticle. An allosteric effector may increase the offload of oxygen from an oxygen carrier to a tissue or cell that is deoxygenated within a subject, and/or increase loading of oxygen onto an oxygen carrier from an oxygenated tissue such as lungs. As such, an allosteric effector may allow oxygen to be bound in the lungs and released in the tissues within the narrow physiological range of partial oxygen pressures from 40-100 mmHg in the deoxygenated tissues and in oxygen-rich lungs. Facile control of $O_2$ affinity is essential to the design of a robust oxygen-carrying nanoparticle, affording ability to tailor nanoparticle design to clinical context. For example, the ability to modulate $O_2$ affinity allows the design of a nanoparticle with increasing $O_2$ affinity suitable for treatment of hypoxia at high altitude, and the design of a nanoparticle with decreasing $O_2$ affinity suitable for treatment of hypoxia at sea level.

A nanoparticle may comprise one allosteric effector or a combination of more than one allosteric effector. Non limiting examples of allosteric effectors capable of modulating the affinity of hemoglobin to oxygen include 2,3-diphosphoglycerate (2,3-DPG) (also known as 2,3-bisphosphoglyceric acid or 2,3-BPG) or an isomer derived therefrom, inositol hexaphosphate (IHP), pyridoxal-phosphate (PLP), or RSR-4, RSR-13 (2-[4-[[(3,5-dimethylanilino carbonyl]methyl]-phenoxy]-2-methylpropionic acid), the structure of which is depicted below.

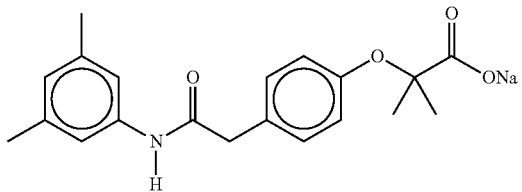

The concentration of allosteric effector in an oxygen-carrying nanoparticle can and will vary, and may be determined experimentally to optimize the oxygen binding and release dynamics of a nanoparticle as described herein. The concentration of 2,3-DPG may be described in terms of a molar ratio to oxygen-carrying agent. The molar ratio of allosteric effector to oxygen-carrying agent may be about 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.00, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, 4.00, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.00, 5.05, 5.10, 5.15, 5.20, 5.25, 5.30, 5.35, 5.40, 5.45, 5.50, 5.55, 5.60, 5.65, 5.70, 5.75, 5.80, 5.85, 5.90, 5.95, 6.00, 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 7.00, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.00, 8.05, 8.10, 8.15, 8.20, 8.25, 8.30, 8.35, 8.40, 8.45, 8.50, 8.55, 8.60, 8.65, 8.70, 8.75, 8.80, 8.85, 8.90, 8.95, 9.00, 9.05, 9.10, 9.15, 9.20, 9.25, 9.30, 9.35, 9.40, 9.45, 9.50, 9.55, 9.60, 9.65, 9.70, 9.75, 9.80, 9.85, 9.90, 9.95, or about 10.00.

Preferably, an allosteric effector is 2,3-DPG. 2,3-DPG may modulate the affinity of an oxygen-carrying agent to oxygen by enhancing responsiveness of an oxygen-carrying nanoparticle to pH. 2,3-DPG may be synthesized by any method known in the art, including chemical synthesis or enzymatic synthesis. See for example, Baer E. "A synthesis of 2,3-diphospho-d-glyceric aid." *J Biol Chem*. 1950; 185: 763-767; or Grisolia S, Joyce BK. "Enzymatic synthesis and isolation of 2,3-diphosphoglycerate." *J Biol Chem*. 1958; 233: 18-19, each hereby incorporated by reference in its entirety. Synthesis may be confirmed by MS and/or NMR.

The concentration of 2,3-DPG in an oxygen-carrying nanoparticle can and will vary, and may be determined experimentally to optimize the oxygen binding and release dynamics of a nanoparticle as described herein. When an oxygen-carrying agent is hemoglobin, the concentration of 2,3-DPG may be about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or about 2 mg/mg hemoglobin. Preferably, the concentration of 2,3-DPG may be about 0.7, 0.8, 0.9, 1, 1.1, 1.2, or about 1.3 mg/mg hemoglobin. Alternatively, the concentration of 2,3-DPG may be described in terms of a molar ratio to hemoglobin. When an oxygen-carrying agent is hemoglobin, the molar ratio of a 2,3-DPG to hemoglobin may be about 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.00, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, 4.00, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.00, 5.05, 5.10, 5.15, 5.20, 5.25, 5.30, 5.35, 5.40, 5.45, 5.50, 5.55, 5.60, 5.65, 5.70, 5.75, 5.80, 5.85, 5.90, 5.95, 6.00, 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 7.00, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.00, 8.05, 8.10, 8.15, 8.20, 8.25, 8.30, 8.35, 8.40, 8.45, 8.50, 8.55, 8.60, 8.65, 8.70, 8.75, 8.80, 8.85, 8.90, 8.95, 9.00, 9.05, 9.10, 9.15, 9.20, 9.25, 9.30, 9.35, 9.40, 9.45, 9.50, 9.55, 9.60, 9.65, 9.70, 9.75, 9.80, 9.85, 9.90, 9.95, or about 10.00.

iii. Reducing Agent

A nanoparticle of the disclosure comprises a reducing agent. When an oxygen-carrying agent is hemoglobin, the hemoglobin may oxidize to methemoglobin, in which the iron in the heme group is in the $Fe^{3+}$ (ferric) state, not the $Fe^{2+}$ (ferrous) of normal hemoglobin. Oxidation of hemoglobin to methemoglobin reduces the affinity of hemoglobin to oxygen and reduces the oxygen-carrying capacity of nanoparticles over time. A reducing agent may prevent oxidation of hemoglobin, regenerate oxidized hemoglobin, or a combination of both. It is contemplated within the scope of this invention that a reducing may prevent oxidation of any oxygen-carrying agents comprising heme. As such, a reducing agent may be capable of maintaining and extending the oxygen-carrying functionality of nanoparticles over a longer period of time, compared to when a reducing agent is not present.

A nanoparticle may comprise one reducing agent or a combination of more than one allosteric effector. Non limiting examples of reducing agents suitable for regenerating oxidized hemoglobin include leucomethylene blue, and derivatives thereof, such as leucobenzyl methylene blue, as well as glutathionine and ascorbate. The concentration of a reducing agent may be sufficient to limit methemoglobin concentrations in a nanoparticle to no more than about 1%, 5%, 6%, 7%, 8%, 9%, 10%, 11%, 12%, 13%, 14%, 15%, 16%, 17%, 18%, 19%, 20% or less of the total concentration of hemoglobin in nanoparticles. Preferably, the concentration of a reducing agent is sufficient to limit methemoglobin concentrations in a nanoparticle to no more than about 8%, 9%, 10%, 11%, 12%, 13%, 14%, or about 15% or less of the total concentration of hemoglobin in nanoparticles. When an oxygen-carrying agent is hemoglobin, the concentration of a reducing agent may be about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, or about 2 mg/mg hemoglobin. Preferably, the concentration of a reducing agent may be about 0.2, 0.3, 0.4, 0.5, 0.6, 0.7, or about 0.8 mg/mg hemoglobin. Alternatively, the concentration of reducing agent may be described in terms of a molar ratio to hemoglobin. When an oxygen-carrying agent is hemoglobin, the molar ratio of a reducing agent to hemoglobin may be about 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.05, 2.10, 2.15, 2.20, 2.25, 2.30, 2.35, 2.40, 2.45, 2.50, 2.55, 2.60, 2.65, 2.70, 2.75, 2.80, 2.85, 2.90, 2.95, 3.00, 3.05, 3.10, 3.15, 3.20, 3.25, 3.30, 3.35, 3.40, 3.45, 3.50, 3.55, 3.60, 3.65, 3.70, 3.75, 3.80, 3.85, 3.90, 3.95, 4.00, 4.05, 4.10, 4.15, 4.20, 4.25, 4.30, 4.35, 4.40, 4.45, 4.50, 4.55, 4.60, 4.65, 4.70, 4.75, 4.80, 4.85, 4.90, 4.95, 5.00, 5.05, 5.10, 5.15, 5.20, 5.25, 5.30, 5.35, 5.40, 5.45, 5.50, 5.55, 5.60, 5.65, 5.70, 5.75, 5.80, 5.85, 5.90, 5.95, 6.00, 6.05, 6.10, 6.15, 6.20, 6.25, 6.30, 6.35, 6.40, 6.45, 6.50, 6.55, 6.60, 6.65, 6.70, 6.75, 6.80, 6.85, 6.90, 6.95, 7.00, 7.05, 7.10, 7.15, 7.20, 7.25, 7.30, 7.35, 7.40, 7.45, 7.50, 7.55, 7.60, 7.65, 7.70, 7.75, 7.80, 7.85, 7.90, 7.95, 8.00, 8.05, 8.10, 8.15, 8.20, 8.25, 8.30, 8.35, 8.40, 8.45, 8.50, 8.55, 8.60, 8.65, 8.70, 8.75, 8.80, 8.85, 8.90, 8.95, 9.00, 9.05, 9.10, 9.15, 9.20, 9.25, 9.30, 9.35, 9.40, 9.45, 9.50, 9.55, 9.60, 9.65, 9.70, 9.75, 9.80, 9.85, 9.90, 9.95, or about 10.00.

iv. Tuning Oxygen-Carrying Nanoparticles

An important feature of a nanoparticle of the disclosure is the physiologic linkage between particle $O_2$ affinity and tissue respiration. While conventional blood substitutes known in the art increase arterial $O_2$ content, the appropriate release of $O_2$ (i.e. along a physiological $O_2$ dissociation curve) by these blood substitutes is infrequently achieved in vivo, due to lack of normal allosteric control of Hb~$O_2$ affinity (expressed as p50, the p $O_2$ at which hemoglobin saturation with $O_2$ (SHb $O_2$) is 50%). The present invention solves this problem with the innovative design of an allosteric effector shuttle-reservoir. To illustrate how the structure of the nanoparticle influences its function, consider a particle comprising hemoglobin as an exemplary oxygen-carrying agent, 2,3-DPG as an exemplary allosteric effector and polyethyleneimine (PEI) as an exemplary branched polymer. The nanoparticle payload contains a heterotropic allosteric effector molecule (2,3-DPG), which modifies Hb $O_2$ affinity; the free concentration of 2,3-DPG in the particle core is modulated by pH-responsive binding to the nanoparticle inner shell—so that 2,3,-DPG is sequestered to the shell during lung perfusion (at high pH, thereby increasing $HbO_2$ affinity and facilitating $O_2$ capture) and 2,3-DPG is released from the shell during systemic perfusion (low pH, thereby lowering $HbO_2$ affinity and facilitating $O_2$ release). This effect is amplified in settings of physiologic need [with lung pathology, hyperventilation raises pH and enhances $O_2$ capture; with tissue hypoxia, anaerobic metabolism lowers pH and enhances $O_2$ release]. As circulatory transit is completed in the lung (or, as hypoxia abates) and pH rises, 2,3-DPG will increasingly re-associate with the shell, thereby: 1) facilitating $O_2$ loading in the lung and 2) linking p50 to tissue $O_2$ debt and its resolution. This physiologically responsive allosteric effector reservoir-shuttle meaningfully differentiates oxygen-carrying nanoparticles of the disclosure from all HBOC designs. Moreover, the design of an oxygen-carrying nanoparticle of the disclosure allows aspects of this shuttle to be refined or "tuned", affording ability to tailor nanoparticle design to clinical context.

Nanoparticles of the disclosure may be tuned to mimic the oxygen-carrying characteristics of red blood cells. Those skilled in the art will appreciate that the oxygen-carrying characteristics of red blood cells may be described by the oxygen-hemoglobin dissociation curve of hemoglobin. The oxygen-hemoglobin dissociation curve plots oxygen saturation ($sO_2$) against partial pressure of oxygen in the blood ($pO_2$), and describes the affinity of hemoglobin for oxygen under physiological conditions of $pO_2$, partial pressure of $CO_2$ ($pCO_2$), pH, temperature, and concentration of allosteric effectors, among other factors. As such, nanoparticles may be tuned to substantially mimic the oxygen-hemoglobin dissociation curve of hemoglobin.

Nanoparticles may be tuned to generate nanoparticles with 50% saturation of the oxygen-carrying agent (p50) of about 10, 15, 20, 25, 30, 35 or about 40 mmHg or more. Preferably, oxygen-carrying nanoparticles are tuned to generate nanoparticles with p50 of about 20 mmHg, 25 mmHg, or about 30 mmHg. Also preferably, oxygen-carrying nanoparticles are tuned to generate nanoparticles with p50 of about 26 mmHg. Methods of tuning p50 of nanoparticles may include tuning the morphology of nanoparticles to increase or decrease the surface area of nanoparticles, tuning the concentration of an oxygen-carrying agent such as hemoglobin in a nanoparticle, tuning the concentration of a reducing agent to limit oxidation of hemoglobin in a nanoparticle, tuning the outer shell of a nanoparticle to control oxygen diffusion into and out of nanoparticles, or combinations thereof.

Nanoparticles may be tuned to enhance the responsiveness of an oxygen-carrying nanoparticle to pH. Responsiveness of hemoglobin to pH, also called the Bohr effect, allows more efficient oxygen binding in the high pH environment of the lungs, and more efficient release of oxygen in the low pH environment of deoxygenated tissue. Methods of enhance the responsiveness of a nanoparticle to pH may include tuning the concentration of an allosteric effector of a nanoparticle. Such an allosteric effector may be 2,3-DPG.

Nanoparticles may be tuned to limit oxidation of hemoglobin to methemoglobin. As described above, nanoparticles may be tuned to limit methemoglobin concentrations in a nanoparticle to no more than about 1%, 5%, 6%, 7%, 8%, 9%, 10%, 11%, 12%, 13%, 14%, 15%, 16%, 17%, 18%, 19%, 20% or less of the total concentration of hemoglobin in nanoparticles. Preferably, oxygen-carrying nanoparticles are tuned to limit methemoglobin concentrations in a nanoparticle to no more than about 8%, 9%, 10%, 11%, 12%, 13%, 14% or about 15% or less of the total concentration of hemoglobin in nanoparticles. Methods of tuning oxidation of hemoglobin may include tuning the morphology of nanoparticles to increase or decrease the surface area of nanoparticles, tuning the concentration of a reducing agent of a nanoparticle, and combinations thereof. Preferably, oxidation of hemoglobin may be tuned by tuning the concentration of a reducing agent such as leucomethylene blue or leucobenzyl methylene blue.

Nanoparticles may also be tuned to limit NO scavenging. NO is an important cellular signaling molecule in mammals and is involved in many physiological and pathological processes. In addition, NO is a powerful vasodilator. Hemoglobin binds NO with an avidity that parallels the binding avidity of hemoglobin to oxygen. Left uncontrolled, a hemoglobin based oxygen carrier may sequester NO, and may lead to vasoconstriction. Methods of tuning oxygen-carrying nanoparticles of the disclosure to limit NO scavenging may include tuning the morphology of nanoparticles to increase or decrease the surface area of nanoparticles exposed to oxygen and NO, tuning the outer shell of a nanoparticle to control NO diffusion into nanoparticles, tuning overall particle size, tuning payload density, or combinations thereof. Those skilled in the art will appreciate that nanoparticles may be tuned to limit NO diffusion into a nanoparticle, but permit oxygen diffusion for oxygen transport. For example, the degree of outer layer cross-linking can be varied to modulate the extent and rate of NO sequestration by the nanoparticle.

Methods of tuning the shell of a nanoparticle may include tuning component ratios of the shell, tuning cross-linking of components of the shell, and tuning pegylation of the shell of nanoparticles. Components of the shell, cross-linking of components of the shell, and pegylation of the shell of nanoparticles may be as described above. Preferably, the shell of a nanoparticle may be tuned by increasing or decreasing the thickness of the shell, increasing or decreasing the hydrophobicity or hydrophilicity of the shell, and increasing or decreasing the level of crosslinking or pegylation of the shell. Further details are provided in the Examples.

(g) Optional Molecules

Bi-concaved disc shaped oxygen-carrying nanoparticles may further comprise at least one molecule selected from the group consisting of a targeting moiety, a biologically active agent, an imaging agent, a metal atom, and a therapeutic agent. A molecule may be water soluble or water insoluble. A molecule may be contained within the aqueous inner core of the nanoparticle, may be conjugated to the surface of the amphiphilic polymer comprising the outer shell of the nanoparticle, may be conjugated within a hydrophilic region of an amphiphilic polymer comprising the outer shell of a nanoparticle, or may be conjugated within a hydrophobic region of an amphiphilic polymer comprising the outer shell of the nanoparticle. It is also envisioned that in nanoparticles comprising more than one optional molecule, molecules may be localized to different locations of the nanoparticle. In general, a targeting moiety will be conjugated to the surface of an amphiphilic polymer comprising the outer shell of the nanoparticle. As used herein, the term "conjugation" refers to either covalent or non-covalent means. Non-covalent means may include ionic bonding, dative bonding, hydrogen bonding, metallic bonding, and so forth, as well as electrostatic, hydrophobic, and van der Waals interactions.

i. Metal Atoms

A variety of metal atoms are suitable for inclusion in nanoparticles. A metal atom may generally be selected from the group of metal atoms comprised of metals with an atomic number of twenty or greater. For instance, metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms.

Metal atoms comprising a nanoparticle may be metal ions. Metal atoms may be in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $Pb^{2+}$, $Pb^{4+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. Metal ions may comprise metal complexes, compounds, or chelates. For example, metal atoms may comprise a complex, chelate, or compound with porphyrin, diethylene triamine pentaacetic acid (DTPA), or tetramethyl heptanedionate (TMHD), 2,4-pentanedione, 1,4,7,10-tetraazacyclododecane-1,4,7,10-tetraacetic acid (DOTA), ethylenediamine-tetraacetic acid disodium salt (EDTA), ethyleneglycol-O,O'-bis(2-aminoethyl)-N, N,N', N'-tetraacetic acid (EGTA), N-(2-hydroxyethyl)ethylenediamine-N,N',N'-triacetic acid trisodium salt (HEDTA), nitrilotriacetic acid (NTA), and 1,4,8,11-tetraazacyclotetradecane-N,N',N'',N'''-tetraacetic acid (TETA). Metal complexes, compounds, or chelates may be organo soluble or water soluble. Non-limiting examples of suitable organo soluble complexes include pentanedione-gadolinium (Ill), bismuthneodecanoate, iohexol and related compounds, and organo soluble complexes of gold. Exemplary water soluble metal chelates or complexes include, but are not limited to, Mn-DTPA, Mn-porphyrin, and Gd-DTPA.

Metal atoms may comprise a metal oxide. For instance, non-limiting examples of metal oxides may include iron oxide, manganese oxide, or gadolinium oxide. Additional examples may include magnetite, maghemite, or a combination thereof. A metal oxide may have the formula $MFe_2O_4$, where M is selected from the group comprising Fe, Mn, Co, Ni, Mg, Cu, Zn, Ba, Sr or a combination thereof. A metal oxide may be magnetic. Preferably, a metal atom may comprise iron oxide. A nanoparticle may also comprise both a metal oxide and an additional metal as described herein. For instance, a nanoparticle may comprise a metal oxide and an additional metal such as iodine, gadolinium, bismuth, or gold. Generally speaking, a metal oxide included in a nanoparticle is between about 1 and about 30 nm in diameter. For example, a metal oxide may be about 1, 2, 3, 4, 5, 10, 15, 20, 25, or 30 nm in diameter.

Typically, a nanoparticle comprises at least 50,000 metal atoms. A nanoparticle may comprise at least 100,000, at least 150,000, at least 200,000, at least 250,000, at least 300,000, at least 350,000, or at least 400,000 metal atoms.

ii. Biologically Active Agent

Oxygen binding nanoparticles may also further comprise at least one biologically active agent in addition to an oxygen-carrying nanoparticle. Non-limiting examples of suitable biologically active agents include pharmaceuticals, therapeutic agents, diagnostic agents, radioactive isotopes, genetic materials, proteins, carbohydrates, lipids, nucleic acid based materials, and combinations thereof. A biologically active agent may be in its native form or it may be derivatized with hydrophobic or charged moieties to enhance incorporation or adsorption to a nanoparticle. Accordingly, a biologically active agent may be water soluble or water insoluble. As detailed above, a biologically active may be contained within the aqueous inner core, conjugated to the surface of the amphiphilic polymer comprising the outer shell, conjugated within the hydrophilic region of the amphiphilic polymer comprising the outer shell, or conjugated within the hydrophobic region of the amphiphilic polymer comprising the outer shell.

Non-limiting examples of biologically active agents may include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. Additionally, a nanoparticle may comprise two or more, three or more, or four or more biologically active agents.

The biologically active agent may also be a targeting moiety (see below). For instance, an antibody, nucleic acid, peptide fragment, small organic molecule, or a mimetic of a biologically active ligand may be a therapeutic agent, such as an antagonist or agonist, when bound to specific epitopes. Thus, a targeting moiety and a therapeutic agent may be constituted by a single component which functions both to target a nanoparticle and to provide a therapeutic agent to the desired site.

The amount of therapeutic agent incorporated into a nanoparticle will vary. Those of skill in the art will appreciate that the loading rate will depend upon the type of therapeutic agent and the intended target, for example.

iii. Targeting Moiety

Bi-concaved disc shaped nanoparticles may also comprise a targeting moiety. A targeting moiety directs or targets the nanoparticle to a particular site or location. Targeted particles may include a wide variety of targeting moieties conjugated to the surface of the outer shell, including, but not limited to, antibodies, antibody fragments, peptides, small molecules, polysaccharides, nucleic acids, aptamers, peptidomimetics, other mimetics, and drugs alone or in combination. Targeting moieties may be utilized to specifically bind the nanoparticles to cellular epitopes and/or receptors. Targeting moieties may be conjugated directly or indirectly to a nanoparticle.

Direct conjugation of targeting moieties to a nanoparticle refers to the preparation of a targeting moiety-nanoparticle complex wherein a targeting moiety is either adsorbed through ionic, electrostatic, hydrophobic or other non-covalent means to the nanoparticle surface (e.g., via an acylated-antibody or hybridization between complementary nucleic acid sequences), or chemically linked to the surface of the outer shell through covalent bonds to a component of the conjugated lipids, or intrinsically incorporated into the amphiphilic polymer of the outer shell (e.g., a lipid derivatized to a peptidomimetic agent). A targeting moiety also may be directly conjugated to a nanoparticle via a linker molecule. A linker molecule comprises at least two functional groups such that the linker molecule is disposed between a nanoparticle and a targeting moiety.

Indirect conjugation refers to forming a complex between a nanoparticle and a targeting moiety in vivo in two or more steps. Indirect conjugation utilizes a chemical linking system to produce the close and specific apposition of the nanoparticle to a targeted cell or tissue surface. A non-limiting example of an indirect targeting system is avidin-biotin.

iv. Imaging Agents

Bi-concaved disc shaped nanoparticles may also comprise an imaging agent. An imaging agent may comprise a metal atom, as detailed above, or may be a radionuclide. Non-limiting examples of suitable radionuclides include technetium-99m, ilodine-123 and 131, thallium-201, gallium-67, fluorine-18, fluorodeoxyglucose, and indium-111. An imaging agent may also be a fluorophore. Suitable fluorophores include, but are not limited to, fluorescein isothiocyante (FITC), fluorescein thiosemicarbazide, rhodamime, Texas Red, CyDyes (e.g., Cy3, Cy5, Cy5.5), Alexa Fluors (e.g., Alexa$^{488}$, Alexa$^{555}$, Alexa$^{594}$; Alexa$^{647}$), and near infrared (NIR) (700-900 nm) fluorescent dyes.

(h) Preferred Embodiments

In some embodiments, a nanoparticle has a substantially bi-concaved disc shape, comprises an aqueous core and a bi-layered shell comprising an amphiphilic polymer, and has a payload comprising an oxygen-carrying agent, an allosteric effector and a reducing agent. The payload is in the interior of the nanoparticle. The amphiphilic polymer comprises a branched amine-containing polymer with reactive groups and is linked to a lipid via the reactive groups, such that at least about 25% of the free reactive groups are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The branched polymer may be a polyethyleneimine branched polymer, a PAMAM dendrimer, a star polymer, or a graft polymer. The lipid may be palmitic acid or C24-pentacosadiynoic acid. The nanoparticle may comprise about 20 to about 60% (w/v) oxygen-carrying agent molecules. The ratio of oxygen-carrying agent to allosteric effector and oxygen-carrying agent to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr).

The nanoparticle may not substantially sequester nitric oxide. The nanoparticle may limit the oxidation of the oxygen-carrying agent to about 10% or less of the total concentration of oxygen-carrying agent in the nanoparticle.

In some embodiments, a nanoparticle has a substantially bi-concaved disc shape, comprises an aqueous core and a bi-layered shell comprising an amphiphilic polymer, and has a payload comprising an oxygen-carrying agent, an allosteric effector and a reducing agent. The payload is in the interior of the nanoparticle. The amphiphilic polymer comprises a branched amine-containing polymer with reactive groups and is linked to a lipid via the reactive groups, such that at least about free 40% of the reactive groups are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The branched polymer may be a polyethyleneimine branched polymer, a PAMAM dendrimer, a star polymer, or a graft polymer. The lipid may be palmitic acid or C24-pentacosadiynoic acid. The nanoparticle may comprise about 20 to about 60% (w/v) oxygen-carrying agent molecules. The ratio of oxygen-carrying agent to allosteric effector and oxygen-carrying agent to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr). The nanoparticle may not substantially sequester nitric oxide. The nanoparticle may limit the oxidation of oxygen-carrying agent to about 10% or less of the total concentration of oxygen-carrying agent in the nanoparticle.

In some embodiments, a nanoparticle has a substantially bi-concaved disc shape, comprises an aqueous core and a bi-layered shell comprising an amphiphilic polymer, and has a payload comprising an oxygen carrying agent, an allosteric effector and a reducing agent. The payload is in the interior of the nanoparticle. The amphiphilic polymer comprises a branched amine-containing polymer with reactive groups and is linked to a lipid via the reactive groups, such that at least about 55% of the free reactive groups are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The branched polymer may be a polyethyleneimine branched polymer, a PAMAM dendrimer, a star polymer, or a graft polymer. The lipid may be palmitic acid or C24-pentacosadiynoic acid. The nanoparticle may comprise about 20 to about 60% (w/v) oxygen-carrying agent molecules. The ratio of oxygen-carrying agent to allosteric effector and oxygen-carrying agent to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr). The nanoparticle may not substantially sequester nitric oxide. The nanoparticle may limit the oxidation of oxygen-carrying agent to about 10% or less of the total concentration of oxygen-carrying agent in the nanoparticle.

In some embodiments, a nanoparticle has a substantially bi-concaved disc shape, comprises an aqueous core and a bi-layered shell comprising an amphiphilic polymer, and has a payload comprising hemoglobin, 2,3-DPG and a reducing agent selected from the group consisting of leucomethylene blue, ascorbate and glutathione. The payload is in the interior of the nanoparticle. The amphiphilic polymer comprises a branched amine-containing polymer with reactive groups and is linked to a lipid via the reactive groups, such that at least about 25% of the free reactive groups are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The branched polymer may be a polyethyleneimine branched polymer, a PAMAM dendrimer, a star polymer, or a graft polymer. The lipid may be palmitic acid or C24-pentacosadiynoic acid. The nanoparticle may comprise about 20 to about 60% (w/v) hemoglobin molecules. The ratio of hemoglobin to allosteric effector and hemoglobin to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr). The nanoparticle may not substantially sequester nitric oxide. The nanoparticle may limit the oxidation of hemoglobin to about 10% or less of the total concentration of hemoglobin in the nanoparticle.

In some embodiments, a nanoparticle has a substantially bi-concaved disc shape, comprises an aqueous core and a bi-layered shell comprising an amphiphilic polymer, and has a payload comprising hemoglobin, 2,3-DPG and a reducing agent selected from the group consisting of leucomethylene blue, ascorbate and glutathione. The payload is in the interior of the nanoparticle. The amphiphilic polymer comprises a branched amine-containing polymer with reactive groups and is linked to a lipid via the reactive groups, such that at least about free 40% of the reactive groups are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The branched polymer may be a polyethyleneimine branched polymer, a PAMAM dendrimer, a star polymer, or a graft polymer. The lipid may be palmitic acid or C24-pentacosadiynoic acid. The nanoparticle may comprise about 20 to about 60% (w/v) hemoglobin molecules. The ratio of hemoglobin to allosteric effector and hemoglobin to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr). The nanoparticle may not substantially sequester nitric oxide. The nanoparticle may limit the oxidation of hemoglobin to about 10% or less of the total concentration of hemoglobin in the nanoparticle.

In some embodiments, a nanoparticle has a substantially bi-concaved disc shape, comprises an aqueous core and a bi-layered shell comprising an amphiphilic polymer, and has a payload comprising hemoglobin, 2,3-DPG and a reducing agent selected from the group consisting of leucomethylene blue, ascorbate and glutathione. The payload is in the interior of the nanoparticle. The amphiphilic polymer comprises a branched amine-containing polymer with reactive groups and is linked to a lipid via the reactive groups, such that at least about 55% of the free reactive groups are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The branched polymer may be a polyethyleneimine branched polymer, a PAMAM dendrimer, a star polymer, or a graft polymer. The lipid may be palmitic acid or C24-pentacosadiynoic acid. The nanoparticle may comprise about 20 to about 60% (w/v) hemoglobin molecules. The ratio of hemoglobin to allosteric effector and hemoglobin to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr). The nanoparticle may not substantially sequester nitric oxide. The nanoparticle may limit the oxidation of hemoglobin to about 10% or less of the total concentration of hemoglobin in the nanoparticle.

In some embodiments, a nanoparticle has a substantially bi-concaved disc shape, comprises an aqueous core and a bi-layered shell comprising an amphiphilic polymer, and has a payload comprising hemoglobin, 2,3-DPG and a reducing agent selected from the group consisting of leucomethylene blue, ascorbate and glutathione. The payload is in the interior of the nanoparticle. The amphiphilic polymer comprises PEI and is linked to a lipid via the reactive groups, such that at least about 40% of the free primary amines are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The PEI may have a MW of 10 kDa to about 100 kDa or more. The lipid may be palmitic acid or C24-pentacosadiynoic acid. The nanoparticle may comprise about 20 to about 60% (w/v) hemoglobin molecules. The ratio of hemoglobin to allosteric effector and hemoglobin to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr). The nanoparticle may not substantially sequester nitric oxide. The nanoparticle may limit the oxidation of hemoglobin to about 10% or less of the total concentration of hemoglobin in the nanoparticle.

In some embodiments, a nanoparticle has a substantially bi-concaved disc shape, comprises an aqueous core and a bi-layered shell comprising an amphiphilic polymer, and has a payload comprising hemoglobin, 2,3-DPG and a reducing agent selected from the group consisting of leucomethylene blue, ascorbate and glutathione. The payload is in the interior of the nanoparticle. The amphiphilic polymer comprises PEI and is linked to a lipid via the reactive groups, such that at least about 50% of the free primary amines are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The PEI may have a MW of 10 kDa to about 100 kDa or more. The lipid may be palmitic acid or C24-pentacosadiynoic acid. The nanoparticle may comprise about 20 to about 60% (w/v) hemoglobin molecules. The ratio of hemoglobin to allosteric effector and hemoglobin to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr). The nanoparticle may not substantially sequester nitric oxide. The nanoparticle may limit the oxidation of hemoglobin to about 10% or less of the total concentration of hemoglobin in the nanoparticle.

In some embodiments, a nanoparticle has a substantially bi-concaved disc shape, comprises an aqueous core and a bi-layered shell comprising an amphiphilic polymer, and has a payload comprising hemoglobin, 2,3-DPG and a reducing agent selected from the group consisting of leucomethylene blue, ascorbate and glutathione. The payload is in the interior of the nanoparticle. The amphiphilic polymer comprises PEI and is linked to a lipid via the reactive groups, such that at least about 55% of the free primary amines are linked to lipids. The surface reactive groups of the amphiphilic polymer comprising the shell are cross-linked with a bifunctional linker. The average diameter of the nanoparticle may be from about 130 nm to about 300 nm, and the average height of the nanoparticle is from about 30 nm to about 80 nm. The nanoparticle may comprise a through-hole or a depression. The PEI may have a MW of 10 kDa to about 100 kDa or more. The lipid may be palmitic acid or C24-pentacosadiynoic acid. The nanoparticle may comprise about 20 to about 60% (w/v) hemoglobin molecules. The ratio of hemoglobin to allosteric effector and hemoglobin to reducing agent may be about independently selected from the group consisting of 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, and 10:1. The nanoparticle design allows the effective release of $O_2$ during perfusion across the $O_2$ tensions/gradients encountered in normal/abnormal human physiology (e.g. tissue $pO_2$ range from 40 to 5 Torr). The nanoparticle may not substantially sequester nitric oxide. The nanoparticle may limit the oxidation of hemoglobin to about 10% or less of the total concentration of hemoglobin in the nanoparticle.

II. Process of Preparing Oxygen-Carrying Nanoparticles

Another aspect of the present disclosure is a process for the preparation of a population of self-assembled, substantially bi-concaved disk shaped nanoparticles. Generally speaking, a process comprises forming an amphiphilic polymer; forming in a non-polar solvent a plurality of inverted micelles comprising the amphiphilic polymer; suspending a payload comprising an oxygen-carrying agent, an allosteric effector, and a reducing agent in a polar solvent and transferring the payload into the organic layer comprising the inverted micelles by agitation; and self-assembly of the inverted micelles into substantially bi-concaved disk shaped nanoparticles. The nanoparticle may be pegylated. Alternatively, the nanoparticle may be cross-linked. In still another alternative, the nanoparticle may be pegylated and cross-linked.

(a) Forming an Amphiphilic Polymer

A process for the preparation of a particle of the disclosure comprises, in part, forming an amphiphilic polymer. Generally speaking, a process comprises hydrophobically modifying a branched polymer by covalently conjugating an amphiphilic lipid to the branched polymer. Suitable branched polymers and amphiphilic lipids are detailed in Section I above. As described above, branched polymers comprise free reactive groups. Free reactive groups may be amine groups.

Generally speaking, at least 25% of free reactive groups of the polymer are linked with amphiphilic lipid. For instance, about 25% to about 55% of free reactive groups of a polymer are linked with lipid, about 30% to about 55% of free reactive groups of a polymer are linked with lipid, about 35% to about 55% of free reactive groups of a polymer are linked with lipid, about 40% to about 55% of free reactive groups of a polymer are linked with lipid, about 45% to about 60% of free reactive groups of a polymer are linked with lipid, about 50% to about 65% of free reactive groups of a polymer are linked with lipid, about 55% to about 70% of free reactive groups of a polymer are linked with lipid, about 60% to about 75% of free reactive groups of a polymer are linked with lipid, about 65% to about 80% of free reactive groups of a polymer are linked with lipid, about 70% to about 85% of free reactive groups of a polymer are linked with lipid, about 75% to about 90% of free reactive groups of a polymer are linked with lipid, about 80% to about 95% of free reactive groups of a polymer are linked with lipid, about 85% to about 100% of free reactive groups of a polymer are linked with lipid. Alternatively, about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 66%, 67%, 68%, 69%, 70%, 71%, 72%, 73%, 74%, 75%, 76%, 77%, 78%, 79%, 80%, 81%, 82%, 83%, 84%, 85%, 86%, 87%· 88%, 89%, 90%, 91%, 92%, 93%, 94%, 95%, 96%, 97%, 98%, 99 or more of free reactive groups of a polymer are linked with lipid. The molar ratio of polymer to lipid is typically from about 1:0.4 to about 1:0.8. In general, molar ratio of polymer to lipid may be about 1:0.4, 1:0.45, 1:0.5, 1:0.55, 1:0.6, 1:0.65, 1:0.7, 1:0.75, or 1:0.8.

Methods of covalently conjugating a lipid to a polymer are known in the art and detailed in the examples. Briefly, an active group of a polymer forms a covalent bond with an active group of a lipid. Suitable polymer active groups are detailed above. A lipid may comprise a suitable active group for forming a bond with a polymer active group (i.e., direct conjugation), or may be treated with a linker to provide a suitable active group (i.e., indirect conjugation). Non-limiting examples of active groups may include epoxides, carboxylates, oxiranes, esters of N-hydroxysuccinimide, aldehydes, hydrazines, maleimides, mercaptans, amino groups, alkylhalides, isothiocyanates, carbodiimides, diazo compounds, tresyl chloride, tosyl chloride, propargyl, azide, and trichloro S-triazine. In general, reactive groups may be photoreactive groups, that when contacted with light may become activated, and capable of covalently attaching to the polymer reactive groups. Exemplary photo-reactive groups may include aryl azides, diazarenes, beta-carbonyldiazo, and benzophenones. Reactive species are nitrenes, carbenes, and radicals. These reactive species are generally capable of covalent bond formation. Preferably, reactive groups are carboxyl and amine.

(b) Forming a Plurality of Inverted Micelles

A process for the preparation of a nanoparticle further comprises, in part, forming a plurality of inverted micelles. Generally speaking, unimolecular inverted micelles (i.e., reversed micelles) are formed by agitating a mixture of an amphiphilic polymer from Section II(a) above with a non-polar solvent. Typically, the concentration of amphiphilic polymer in a non-polar solvent is about $10^{-7}$ to about $10^{-5}$ M. In general, the concentration of amphiphilic polymer is about $10^{-6}$ M.

The non-polar solvent may be organic. Non-limiting examples of non-polar solvents may include acetone, methyl acetate, ethyl acetate, hexane, benzene, toluene, diethyl ether, dichloromethane, and chloroform. An exemplary solvent may be chloroform or dichloromethane.

A mixture may be agitated through physical inversion, vortexing, mixing, shaking, sonicating, stirring, or other similar means. Typically, a mixture may be agitated for about 1 minute to about 10 minutes, although longer agitation times may be possible. A mixture may be agitated for about 1, 2, 3, 4, 5, 6, 7, 8, 9, 10 minutes or more. Generally speaking, the agitation is performed at about 4° C. to about room temperature.

(c) Transfer of the Payload into the Organic Layer Comprising the Inverted Micelles A nanoparticle comprises a payload, the payload comprising an oxygen-carrying agent, an allosteric effector, and a reducing agent. An oxygen-carrying agent, an allosteric effector, and a reducing agent may be as described in Section I(f) above. A payload is mixed with an aqueous solvent and the mixture is added to the non-polar solvent mixture of the inverted micelles resulting in a bi-phasic mixture. The bi-phasic mixture is allowed to settle down, if needed, and then the payload is transferred to the organic layer comprising the inverted micelles by agitation. Typically, only minimal agitation is required, and physical inversion and/or swirling or shaking is sufficient to transfer an oxygen-carrying agent, an allosteric effector, and a reducing agent to the interior of the inverse micelles. Agitation may also be by high shear mixing. Non-limiting examples of high-shear mixing may include microfluidization, sonication, homogenization, or related mixing. An aqueous solvent may be the polar solvent described in Section II(d).

(d) Self-Assembly of a Bi-Concaved Disc Shaped Nanoparticle

After formation of a plurality of inverted micelles comprising the payload in Section II(c) above, a process of the disclosure comprises self-assembly of inverted micelles into a substantially bi-concaved disc shaped nanoparticle. Generally speaking, a process comprises agitating inverted micelles in the presence of heat and a solvent system.

The temperature during the agitating dictates, in part, the size of resulting nanoparticles. Typically, as the temperature increases, the size of nanoparticles increases. The temperature during the agitation may range from about 30° C. to about 65° C. For instance, the temperature may be about 30, 35, 40, 45, 50, 55, 60, or 65° C.

A mixture may be agitated via physical or acoustical means. For instance, a mixture may be agitated by physical inversion, vortexing, mixing, shaking, sonicating, or other similar means. Preferably, a mixture may be agitated by high shear mixing. Generally, the inverted micelles are agitated for about 15 min to about 90 min, for about 30 min to about 60 min, or for about 20, 25, 30, 35, 40, 45, 50, 55, 60, 65 or 70 min.

Inverted micelles are typically agitated, with heat, in the presence of a solvent system. A solvent system comprises both a polar solvent and a non-polar solvent. For instance, a polar solvent is an aqueous solvent and a non-polar solvent is an organic solvent. By way of example, a non-polar solvent may be the non-polar solvent used in Section II(b) above, and an aqueous solvent may be added, with brief agitation, to the non-polar solvent. To achieve an appropriate ratio between a polar and non-polar solvent, a non-polar solvent may be evaporated from the mixture. The weight ratio of a polar and non-polar solvent may be about 1:5. An exemplary polar solvent may be methanol and an exemplary non-polar solvent may be chloroform.

To achieve an appropriate ratio between a polar and non-polar solvent, the non-polar solvent may be evaporated from the mixture. The evaporation may be performed under reduced pressure. Generally speaking, the pressure selected will depend, in part, on the non-polar solvent. The reduced pressure may be between about 350 mbar and 1000 mbar, or about 400, 450, 500, 550, 600, 650, 700, 750, 800, 850, 900, or 950 mbar. When a non-polar solvent is chloroform, the reduced pressure may be between about 400 and about 500 mbar. For instance, the reduced pressure may be between about 400 mbar and about 450 mbar, or between about 420 mbar and about 440 mbar.

(e) Optional Molecules

A nanoparticle may further comprise at least one molecule selected from the group consisting of a targeting moiety, a biologically active agent, a contrast agent, a metal atom, and a therapeutic agent. Suitable molecules are detailed above. These molecules may be conjugated to the surface of the shell of a nanoparticle or contained in the interior of the nanoparticle.

Molecules may be incorporated into the shell of a nanoparticle. To incorporate such a molecule, a targeting moiety, biologically active agent, imaging agent, metal atom, or therapeutic agent is typically added to a mixture comprising a plurality of inverted micelles in a non-polar solvent described in Section II(b) above. After mixing, a molecule is incorporated into micelles by phase transition from aqueous to organic phase. As a result, after self-assembly, a molecule is incorporated into the shell of the nanoparticle.

A water soluble biologically active agent, imaging agent, metal atom, or therapeutic agent may be incorporated into the aqueous core of a nanoparticle. To incorporate such a molecule, a biologically active agent, imaging agent, metal atom, or therapeutic agent may be transferred to the interior of an inverted micelle. For instance, after formation of a plurality of micelles, but before the self-assembly of nanoparticles, the plurality of micelles may be mixed with the water soluble molecule. The mixture may be agitated, and as a result, a water soluble molecule is transferred to the interior of inverted micelles, and consequently, to the aqueous core of a nanoparticle after the self-assembly of the inverted micelles. Typically, only minimal agitation is required, and physical inversion is sufficient to transfer a water soluble molecules to the interior of inverse micelles.

A water insoluble targeting moiety, metal atom, biologically active agent, imaging agent, or therapeutic agent may also be located within a hydrophobic region of an amphiphilic polymer comprising the shell of a nanoparticle. To incorporate such a molecule, a water insoluble molecule may be dissolved in organic non polar solvent and mixed with the inverted micelles. Consequently, a water insoluble molecule is transferred to the hydrophobic region of the amphiphilic polymer after the self-assembly of inverted micelles.

A targeting moiety, biologically active agent, imaging agent, metal atom, or therapeutic agent may be located within the hydrophilic region of the amphiphilic polymer or the surface of the outer of a nanoparticle. A molecule may be adsorbed to the surface through non-covalent bonds, or covalently bonded to the amphiphilic polymer. For instance, a molecule may be bonded to the surface of the nanoparticle through covalent bonding, dative bonding, ionic bonding, hydrogen bonding or Van der Waals bonding.

(f) Cross-Linking

After the self-assembly of a nanoparticle, the shell may be cross-linked. As detailed above, cross-linking may be used to alter the rate of release of oxygen and therapeutic molecules. Alternatively, cross-linking may be used to increase the stability of a nanoparticle. The particles may be cross-linked on the surface of the outer shell, or may be cross-linked within the outer shell. The cross-linking may be chemical cross-linking or photochemical cross-linking. Methods of cross-linking are known in the art. Briefly, suitable cross-linkers will react with one or more active groups of the amphiphilic polymer. Cross-linkers may be homobifunctional or heterobifunctional. Cross-linkers may be chemical cross-linkers or non-chemical cross-linkers. Suitable chemical cross-linkers may include glutaraldehyde, bis-carboxylic acid spacers, or bis-carboxylic acid-active esters. Photochemical cross-linking may be achieved by uv-crosslinking of polydiacetylinic bonds. One of ordinary skill in the art would recognize that a suitable cross-linker can and will vary depending on a composition of a nanoparticle and the intended use.

(g) PEGylation

A particle of the disclosure may be pegylated. As used herein, "pegylation" refers to the addition of polyethylene glycol to the outer shell. Methods of pegylation are commonly known in the art and detailed in the examples. The pegylation may be used to decrease the zeta surface charge of the nanoparticle. Stated another way, pegylation may be used to impart a near neutral surface of a nanoparticle. The pegylation may be used to alter the in vivo circulation of a nanoparticle.

(h) Sterilization and Lyophilization

Sterility of nanoparticle compositions are important for in vivo applications. Sterilization may be accomplished through any method known in the art, provided the method does not materially affect particle stability and/or O2 binding/release. For example, nanoparticles compositions or solutions may be filtered sterilized through membranes with a pore size of 0.22 μm or less. Non-limiting examples of suitable membranes include hydrophobic polytetrafluoroethylene, hydrophilic Durapore® (polyvinylidene fluoride) and polyethersulfone. Filtration efficiency may be determined for each membrane by comparing applied and recovered volumes, particle size, and/or zeta potential.

Nanoparticle aliquots in buffered suspension may be dried to a powder and sealed under an inert gas as the lyophilized powder with or without a cryoprotectant. Preferably, suspensions of aliquots are lyophilized, though other methods known in the art may be used. Suitable inert gases are known in the art and may include, but are not limited to, argon. Similarly, suitable cyroprotectants are known in the art and may include, but are not limited to sorbitol. Reconstituted aliquots may be evaluated for altered particle size, zeta potential, pH, viscosity, sterility, and/or $O_2$ dissociation as described herein. Accepted storage conditions, expiration dating, and release specifications will reflect less than 20%, more preferably less than 15%, even more preferably less than 10% change from baseline properties. The lyophilized powder may be reconstituted in a fashion that is tailored for the intended use, and/or the status of patients' circulating blood volume. For example, a blood substitute composition comprising a nanoparticle of the disclosure may be composed in a more concentrated fashion to be administered to normovolemic patients with anemia or in a more dilute fashion to be administered to hypovolemic patients with hemorrhage.

III. Blood Substitute Compositions Comprising Nanoparticles

A further aspect of the disclosure encompasses blood substitute compositions comprising nanoparticles of the disclosure. Typically, nanoparticles are formulated as a composition for use as a blood substitute for in vivo, in vitro, in situ, or ex vivo use.

Blood substitute nanoparticles may be formulated by mixing nanoparticles with optional excipients and a suitable diluent. The concentration of nanoparticles in the diluent may vary according to the application. Preferably, the concentration of nanoparticles may be about $4 \times 10^{12}$-$6 \times 10^{12}$ nanoparticles/ml.

A composition comprising a plurality of nanoparticles may be a dry powder such as a lyophilized composition comprising nanoparticles. Alternatively, a composition comprising a plurality of nanoparticles may be a solution, a mixture, or a suspension. A non-limiting example of a suspension is a colloid. Generally speaking a colloid is a suspension of fine particles that do not readily settle out of the suspension. A dry powder may be formed of nanoparticles in accordance with known techniques such as freeze drying or lyophilization. A dry powder comprising nanoparticles may then be reconstituted by mixing with an aqueous solution to produce a liquid blood substitute.

The composition may be formulated and administered to a subject by several different means that will supplement the oxygen-carrying capacity of a subject's blood. Such compositions may generally be administered intravascularly in dosage unit formulations containing conventional nontoxic pharmaceutically acceptable carriers, adjuvants, excipients, and vehicles as desired.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, Lactate Ringer's solutions, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

IV. Methods of Using Oxygen-Carrying Nanoparticles

Another aspect of the disclosure encompasses methods of using the bi-concaved shaped oxygen-carrying nanoparticles of the disclosure. In essence, an oxygen-carrying nanoparticles are capable of delivering oxygen. As such, oxygen-carrying nanoparticles may be used to deliver oxygen to a subject in need of a rapid restoration of $O_2$ levels or an increased $O_2$ level, or a replacement of $O_2$ levels is clinically indicated. Oxygen-carrying nanoparticles may be used to supplement the oxygen-carrying capacity of a subject's blood, to treat a subject in need of blood, or to conduct blood transfusion in a patient. Typically, nanoparticles are formulated as a composition for in vivo, in vitro, in situ, or ex vivo use as described in Section III above.

A composition of nanoparticles may be administered to a subject to deliver oxygen to a biological tissue. Suitable subjects include, but are not limited to, mammals, amphibians, reptiles, birds, and fish. Suitable mammals include, but are not limited to, humans, horses, cats and dogs.

Biological tissue, as used herein, may refer to cells, organs, tumors, or material associated with cells, organs, or tumors, such as blood clots. Suitable tissues may include, but are not limited to, heart, lungs, brain, eye, stomach, spleen, bones, pancreas, gall bladder, kidneys, liver, intestines, skin, uterus, bladder, eyes, lymph nodes, blood vessels, and blood and lymph components.

The numerous settings in which oxygen delivery using oxygen-carrying nanoparticles of the disclosure find use include the following:

Trauma.

An acute loss of whole blood can result in a fluid shift from the interstitial and intracellular spaces to replace the lost volume of blood while shunting of blood away from the low priority organs including the skin and gut. Shunting of blood away from organs reduces and sometimes eliminates $O_2$ levels in these organs and results in progressive tissue death.

Ischemia.

In ischemia, a particular organ (or organs) are "starved" for oxygen. Small sections of the organ, known as infarcts, begin to die as a result of the lack of $O_2$. Rapid restoration of $O_2$ levels is critical is stemming infarct formation in critical tissues. Conditions resulting in ischemia include heart attack, stroke, or cerebrovascular trauma.

Hemodilution:

In this clinical application, a blood substitute is required to replace blood that is removed pre-operatively. It is contemplated that patient blood removal occurs to prevent a requirement for allogeneic transfusions post-operatively. In this application, the blood substitute is administered to replace (or substitute for) the $O_2$ levels of the removed autologous blood. This permits the use of the removed autologous blood for necessary transfusions during and after surgery. One such surgery requiring pre-operative blood removal would be a cardiopulmonary bypass procedure.

Septic Shock.

In overwhelming sepsis, some patients may become hypertensive in spite of massive fluid therapy and treatment with vasocontrictor agents. In this instance, the overproduction of nitric oxide (NO) results in the lowered blood pressure. Therefore hemoglobin is close to an ideal agent for treatment of these patients because hemoglobin binds NO with an avidity that parallels $O_2$.

Cancer.

Delivery of $O_2$ to the hypoxic inner core of a tumor mass increases its sensitivity to radiotherapy and chemotherapy. Because the microvasculature of a tumor is unlike that of other tissues, sensitization through increasing $O_2$ levels requires $O_2$ be unloaded within the hypoxic core. In other words, the p50 should be very low to prevent early unloading of the $O_2$, increasing the $O_2$ levels, to insure optimal sensitization of the tumor to subsequent radiation and chemotherapy treatments.

Chronic Anemia.

In these patients, replacement of lost or metabolized hemoglobin is compromised or completely absent. It is contemplated that the blood substitute must effectively replace or increase the reduced $O_2$ levels in the patient.

Sickle Cell Anemia.

In sickle cell anemia, the patient is debilitated by a loss of 02 levels that occurs during the sickling process as well as a very high red blood cell turnover rate. The sickling process is a function of $pO_2$ where the lower the $pO_2$, the greater the sickling rate. It is contemplated that the ideal blood substitute would restore patient $O_2$ levels to within a normal range during a sickling crisis.

Cardioplegia.

In certain cardiac surgical procedures, the heart is stopped by appropriate electrocyte solutions and reducing patient temperature. Reduction of the temperature will significantly reduce the p50, possibly preventing unloading of $O_2$ under any ordinary physiological conditions. Replacement of $O_2$ levels is contemplated as potentially reducing tissue damage and death during such procedures.

Hypoxia.

Soldiers, altitude dwellers, and world-class athletes under extreme conditions may suffer reduced $O_2$ levels because extraction of 02 from air in the lung is limited. The limited $O_2$ extraction further limits $O_2$ transport. It is contemplated that a blood substitute could replace or increase the $O_2$ levels in such individuals.

Organ Perfusion.

During the time an organ is maintained ex vivo, maintaining $O_2$ content is essential to preserving structural and cellular integrity and minimizing infarct formation. It is contemplated that a blood substitute would sustain the $O_2$ requirements for such an organ.

Cell Culture.

This requirement is virtually identical to that of organ perfusion, except that the rate of $O_2$ consumption may be higher.

Hematopoiesis.

It is contemplated that the blood substitute serves as a source for heme and iron for use in the synthesis of new hemoglobin during hematopoiesis.

The present disclosure may also be used in non-humans. The methods and compositions of the present disclosure may be used with domestic animals such as livestock and companion animals (e.g., dogs, cats, horses, birds, reptiles), as well as other animals in aquaria, zoos, oceanaria, and other facilities that house animals. It is contemplated that the present disclosure finds utility in the emergency treatment of domestic and wild animals suffering a loss of blood due to injury, hemolytic anemias, etc. For example, it is contemplated that embodiments of the present disclosure are useful in conditions such as equine infectious anemia, feline infectious anemia, hemolytic anemia due to chemicals and other physical agents, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic, parasitism, etc. In particular, the present disclosure finds use in areas where blood donors for animals of rare and/or exotic species are difficult to find.

Definitions

As used herein, the term "allosteric effector" refers to a molecule that modulates the rate or amount of oxygen binding to or releasing from of an oxygen carrier.

The phrase "exterior of a nanoparticle", as used herein, refers to the outer layer of the nanoparticle shell and any component(s) attached covalently or non-covalently to the outer layer of the nanoparticle shell, or any component(s) within the outer layer of the nanoparticle shell. For example, the exterior of a nanoparticle may also comprise an optional molecule.

The term "hemoglobin" is used herein to generally refer to a protein that may be contained within a red blood cell that transports oxygen. Each molecule of hemoglobin has 4 subunits, 2 $\alpha$ chains and 2 $\beta$ chains, which are arranged in a tetrameric structure. Each subunit also contains one heme group, which is the iron-containing center that binds oxygen. Thus, each hemoglobin molecule can bind 4 oxygen molecules. "Hemoglobin" refers to naturally occurring or synthetic hemoglobin. Hemoglobin may be isolated and purified from a human or animals, or may be produced by chemical synthesis and recombinant techniques.

The term "hemoglobin free of stroma", as used herein, refers to hemoglobin from which all red blood cell membranes have been removed.

The term "hemodynamic parameters", as used herein, refers broadly to measurements indicative of blood pressure, flow and volume status, including measurements such as blood pressure, cardiac output, right atrial pressure, and left ventricular end diastolic pressure.

The phrase "interior of a nanoparticle", as used herein, refers to the any portion of the nanoparticle that is not the exterior of the nanoparticle. The interior of a nanoparticle comprises the inner layer of the nanoparticle shell, the hydrophobic region between the inner and outer layer of the nanoparticle shell, the aqueous core and the payload. The interior of a nanoparticle may also comprise an optional molecule.

The term "methemoglobin", as used herein, refers to an oxidized form of hemoglobin that contains iron in the ferric state and cannot function as an oxygen carrier.

The term "perfluorocarbons", as used herein, refers to synthetic, inert, molecules that contain fluorine atoms, and that consist entirely of halogen (Br, F, CI) and carbon atoms. In the form of emulsions, they are under development as blood substances, because they have the ability to dissolve many times more oxygen than equivalent amounts of plasma or water.

The term "modified hemoglobin" includes, but is not limited to, hemoglobin altered by a chemical reaction such as intra- and inter-molecular cross-linking, genetic manipulation, polymerization, and/or conjugation to other chemical groups (e.g., polyalkylene oxides, for example polyethylene glycol, or other adducts such as proteins, peptides, carbohydrates, synthetic polymers and the like). In essence, hemoglobin is "modified" if any of its structural or functional properties have been altered from its native state. As used herein, the term "hemoglobin" by itself refers both to native, unmodified, hemoglobin, as well as modified hemoglobin.

The terms "nanoparticle" and "oxygen-carrying nanoparticle" used interchangeably throughout the application.

The term "oxygen affinity" refers to the avidity with which an oxygen carrier such as hemoglobin binds molecular oxygen. This characteristic is defined by the oxygen equilibrium curve which relates the degree of saturation of hemoglobin molecules with oxygen (Y axis) with the partial pressure of oxygen (X axis). The position of this curve is denoted by the value, p50, the partial pressure of oxygen at which the oxygen carrier is half-saturated with oxygen, and is inversely related to oxygen affinity. Hence the lower the p50, the higher the oxygen affinity. The oxygen affinity of whole blood (and components of whole blood such as red blood cells and hemoglobin) can be measured by a variety of methods known in the art. (See, e.g., Winslow et al., J. Biol. Chem. 252(7):2331-37 (1977)). Oxygen affinity may also be determined using a commercially available HEMOX™ Analyzer (TCS Scientific Corporation, New Hope, Pa.). (See, e.g., Vandegriff and Shrager in "Methods in Enzymology" (Everse et al., eds.) 232:460 (1994)).

The term "oxygen-carrying capacity," or simply "oxygen capacity" refers to the capacity of a blood substitute to carry oxygen, but does not necessarily correlate with the efficiency in which it delivers oxygen. Oxygen-carrying capacity is generally calculated from hemoglobin concentration, since it is known that each gram of hemoglobin binds 1.34 ml of oxygen. Thus, the hemoglobin concentration in g/dl multiplied by the factor 1.34 yields the oxygen capacity in ml/dl. Hemoglobin concentration can be measured by any known method, such as by using the β-Hemoglobin Photometer (HemoCue, Inc., Angelholm, Sweden). Similarly, oxygen capacity can be measured by the amount of oxygen released from a sample of hemoglobin or blood by using, for example, a fuel cell instrument (e.g., Lex-O2-Con; Lexington Instruments).

The term "oxygen-carrying component" refers broadly to a substance capable of carrying oxygen in the body's circulatory system and delivering at least a portion of that oxygen to the tissues. The oxygen-carrying component may be native or modified hemoglobin, and may also be referred to herein as a "hemoglobin based oxygen carrier," or "HBOC".

The term "payload" refers to the components contained within the interior of a nanoparticle. A payload comprises an oxygen-carrying agent, an effector agent, and a reducing agent. A payload may further comprise optional molecules.

The terms "shell" and "bi-layered shell" are used interchangeably, and generally refer to the shell of a nanoparticle. A shell is bi-layered, comprised of a hydrophilic outer layer, a hydrophilic inner layer, and a hydrophobic region between the layers.

Having described the disclosure in detail, it will be apparent that modifications and variations are possible without departing from the scope of the disclosure defined in the appended claims.

EXAMPLES

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Preparation of Nanoparticles

Figure 1A:
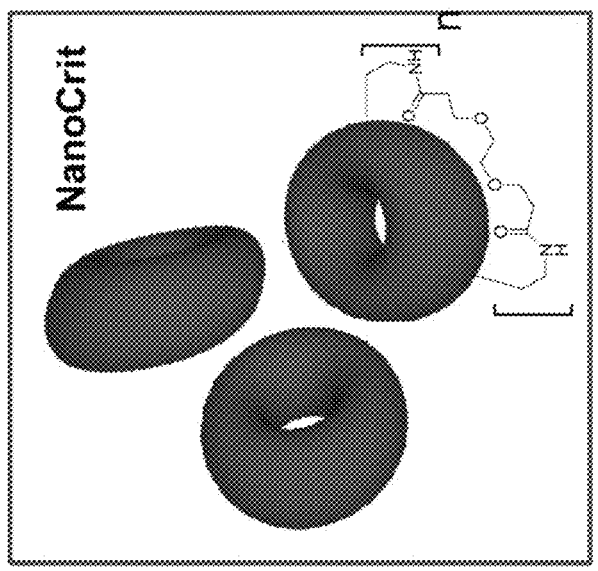
FIG. 1A-F depicts the preparation and various characteristics of nanoparticles comprising hemoglobin. (A) Schematic representation of nanoparticle preparation and schematic representation of nanoparticles. (B) A plot showing the variation of nanoparticle sizes in a preparation of nanoparticles. (C) A plot showing the variation of particle size of lyophilized and non-lyophilized nanoparticles with time. (D) Transmission electron microscope image of nanoparticles drop-deposited over nickel grid. (E) Magnified view of squared-off portion of transmission electron microscope image of nanoparticles in D. (F) Atomic force microscope image of nanoparticles.
Figure 1A:
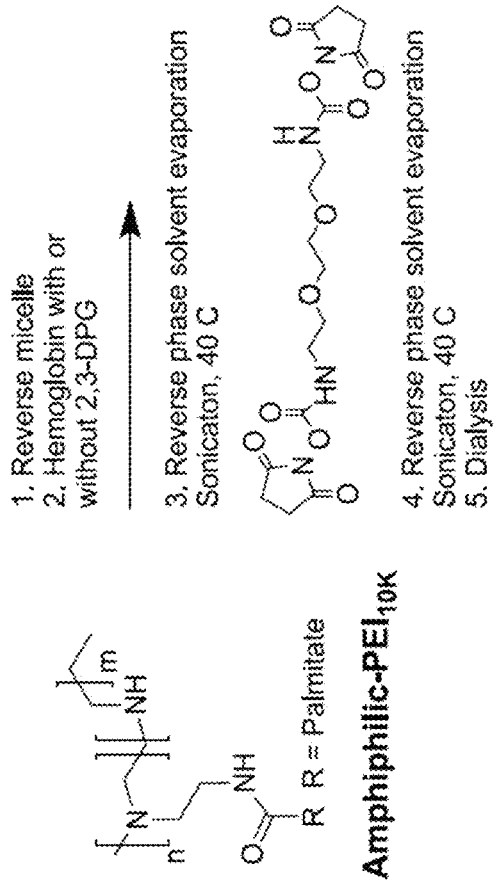
Figure 1B:
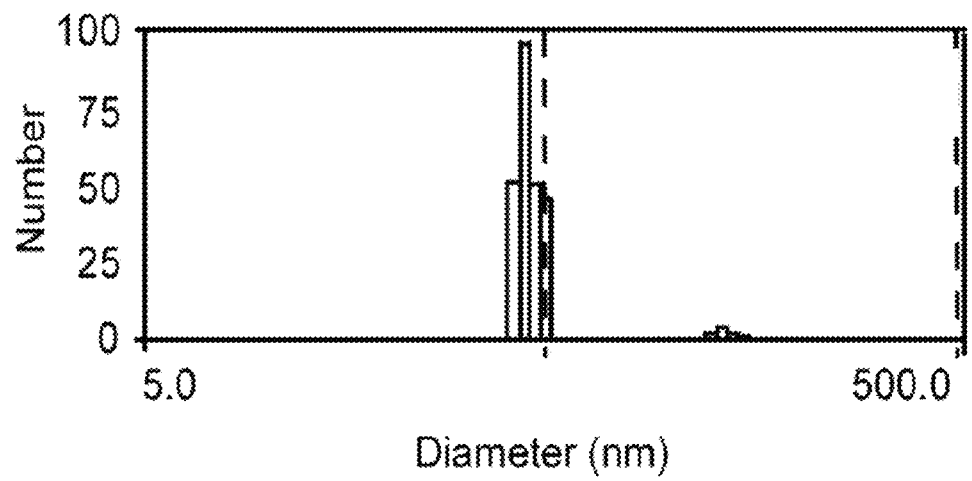
Figure 1C:
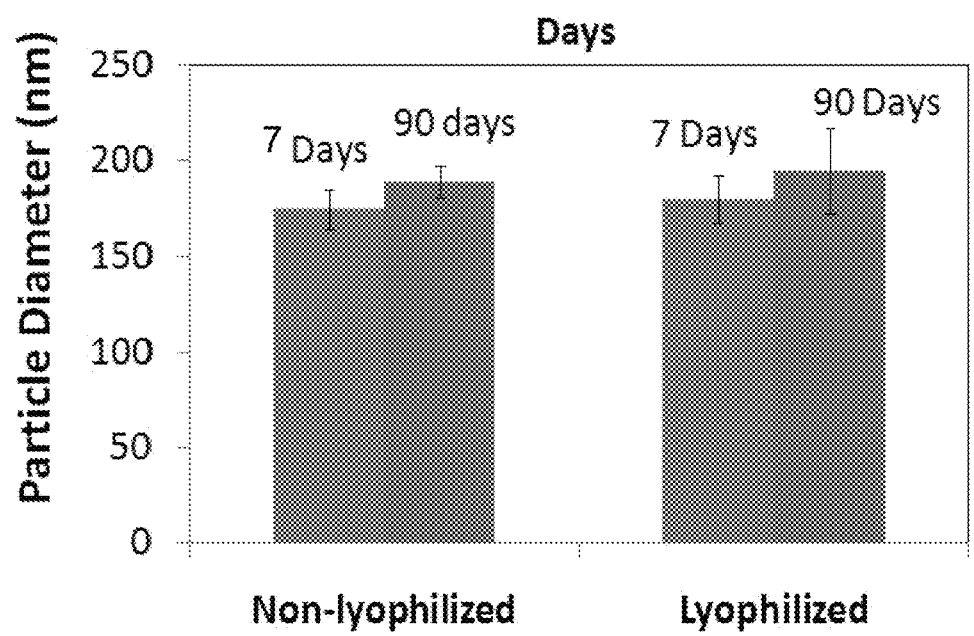
Figure 1D:
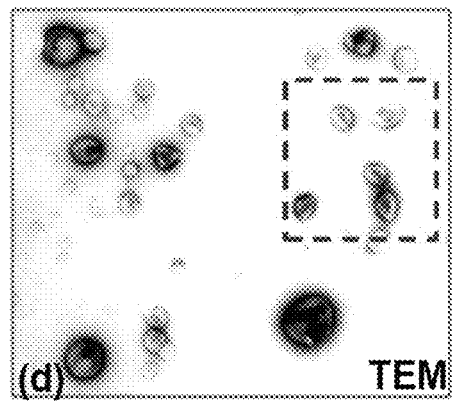
Figure 1:
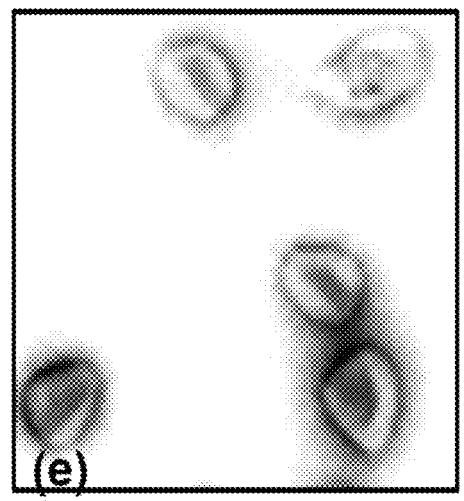
Figure 1F:
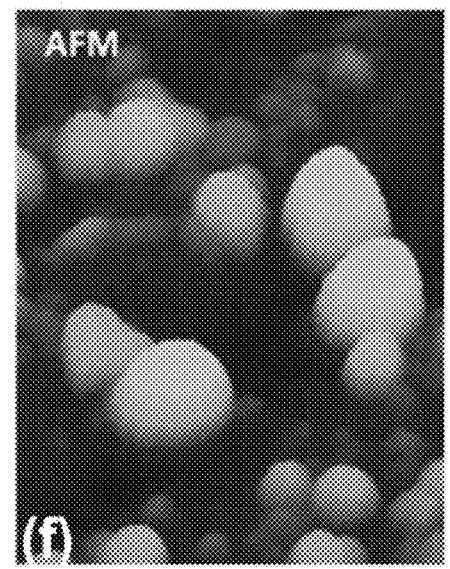
Figure 2A:
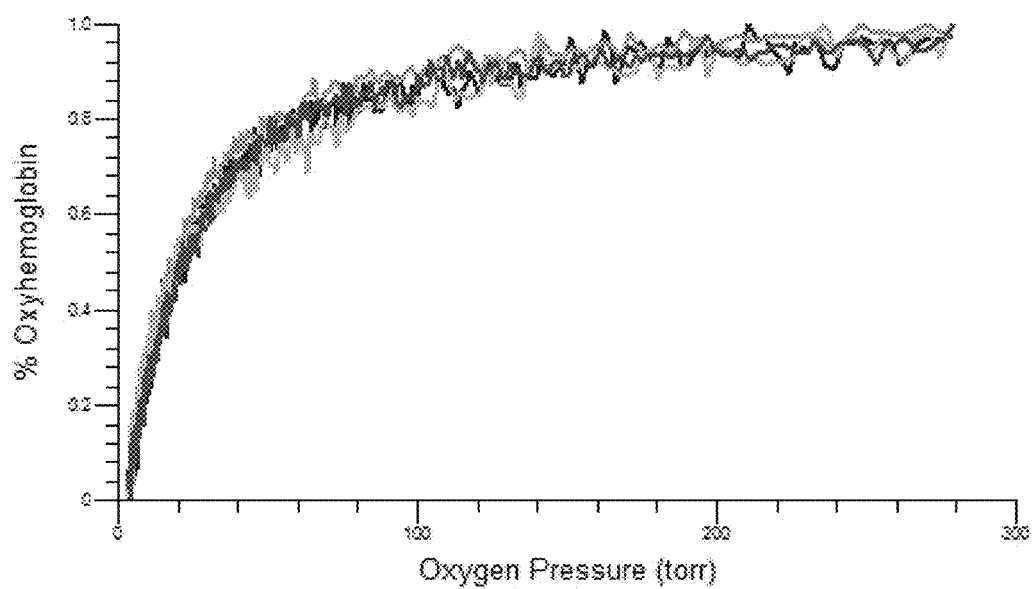
FIG. 2A-D depicts oxygen binding-dissociation curves of nanoparticles measured at pH 10 (dark blue curves), 9 (green curves), 8.5 (magenta curves), 8 (light blue curves), and 6
Figure 2B:
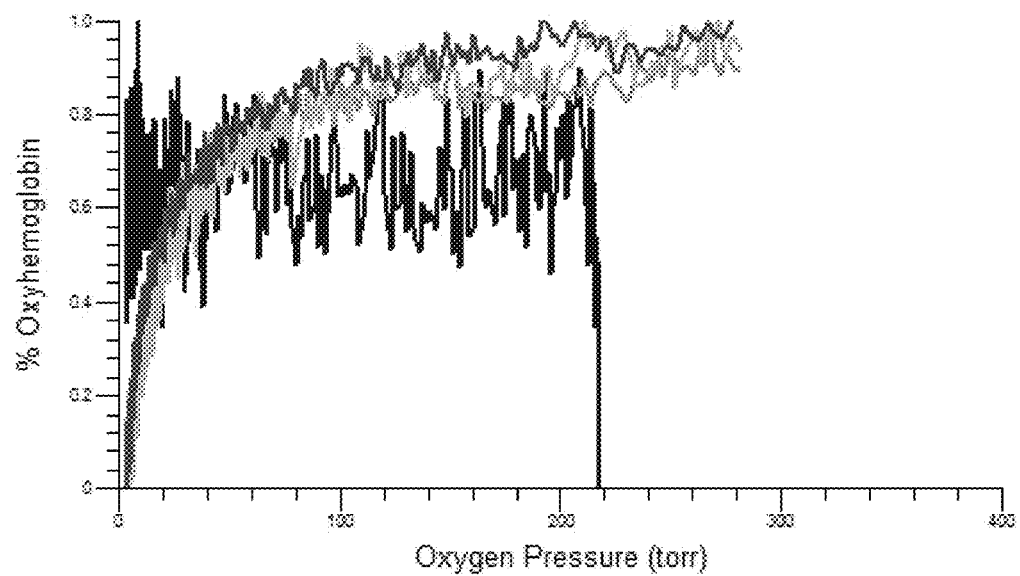
Figure 2C:
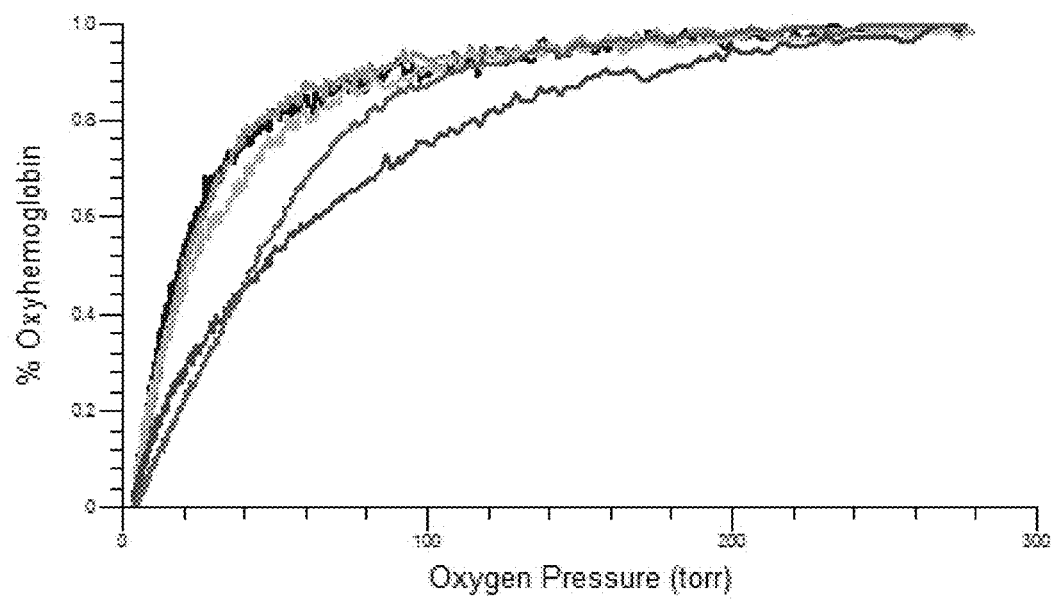
Figure 2D:
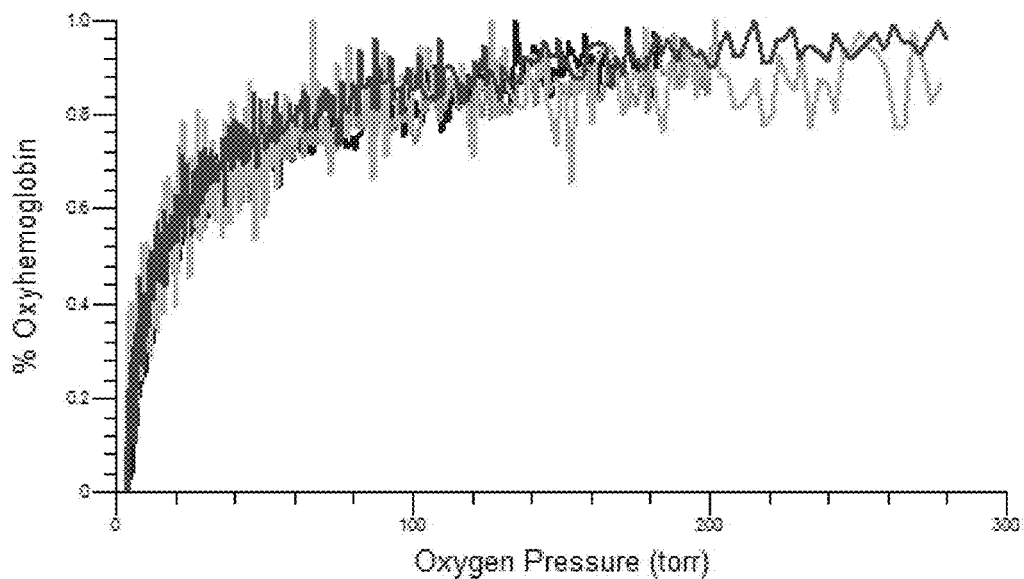

Preparation and loading of biconcave nanoparticles is as described in Pan et al., 2008 J Am Chem Soc 130:9186-9187, PCT Application No. PCT/US2008/079414, and US Publication No. 2010/0297007, all of which are incorporated herein in their entirety. A schematic representation of the particles and preparation of the nanoparticles is shown in FIG. 1.

Polyethyleneimine polymers were grafted with hydrophobic alkyl groups by covalent means. Palmitic acid was activated with the carbodiimide EDAC (1-ethyl-3-(3-dimethylaminopropyl) carbodiimide, hydrochloride) followed by addition of the polymer to achieve greater than 50% functionalization of free primary amine groups. The amphiphilic polymer assumes a 7-10 nm sized unimolecular inverted micellar structure in organic solvent after vortexing.

Hemoglobin, hemoglobin and 2,3-DPG, or hemoglobin, 2,3-DPG, and leucomethylene blue or leucobenzyl methylene blue were loaded into the nanoparticles. Nanoparticles are loaded by adding solutions comprising hemoglobin, hemoglobin and 2,3-DPG, or hemoglobin, 2,3-DPG, and leucomethylene blue or leucobenzyl methylene blue to an aqueous suspension of nanoparticles, followed by briefly shaking/swirling.

Hemoglobin was human hemoglobin extracted and purified from expired RBCs. Hemoglobin was stabilized as carboxyhemoglobin (HbCO), purified via ion-exchange chromatography, and concentrated using ultrafiltration to 4.0 g/dL. The concentration of hemoglobin used to generate the nanoparticles was 10 mg/mL. The concentration of 2,3-DPG was 10 mg/mL. The concentration of leucomethylene blue or leucobenzyl methylene blue was 5 mg/mL. The nanoparticles comprised an average of 3488 hemoglobin molecules per nanoparticle.

Nanoparticle sizes, shape, and morphology were measured by TEM, DLS, and AFM among other methods. Nanoparticles had a hydrodynamic diameter of 150-180 nm, or 173±10 nm after re-suspension, with polydispersity of 0.26±0.01, and zeta potential of ~12±2 mV. Assays were performed as described in Pan D, Caruthers S D, Hu G, Senpan A, Scott M J, Gaffney P J, Wickline S A, Lanza G M. Ligand-directed nanobialys as theranostic agent for drug delivery and manganese-based magnetic resonance imaging of vascular targets. J Am Chem Soc. 2008; 130:9186-9187.

Following self-assembly, surface chemical cross-linking is achieved using Sulfo-EGS (ethylene glycol bis[sulfosuccinimidylsuccinate], PBS, pH 8.5) in combination with hydroxylamine for 5 h at 37° C. Crosslinking has limited effect on particle size and zeta potential: 167±56 nm, +7±2 mV, respectively.

Example 2. Oxygen Binding Characteristics of Labeled and Unlabeled Nanoparticles Nanoparticles produced labeled with leucobenzyl methylene blue or unlabeled nanoparticles were resuspended in water, and used for characterization of oxygen binding characteristics. Nanoparticles were produced generally as described in Example 1. The resulting solution had a total concentration of $5 \times 10^{12}$ nanoparticles/ml, and 2 g/l of glycated hemoglobin.

A Hemox Analyzer was used to characterize oxygen binding-dissociation of the nanoparticles at pH10, 8, 6, and pH8.5. All measurements were generated at 37.3° C. In general, non-labeled particles exhibited significantly higher p50 (lower affinity for oxygen) at low pH than labeled nanoparticles (FIG. 2 and Table 1).

At all pH measurements, p50 of nanoparticles are generally lower than the p50 of human blood, which is typically 26.6 mm Hg (53.2 mm Hg in these readings). A generally lower p50 indicates a higher affinity for oxygen. A Bohr effect (right shift with decreased pH) was observed for non-labeled nanoparticles, but not for labeled nanoparticles. In addition, oxygen binding-dissociation curves were measured using freshly prepared nanoparticles, and particles that were in storage for about one month. In short, older hemoglobin generates oxygen binding-dissociation curves with more noise in the recordings (FIG. 2).

TABLE 1

| pH | p50 mmHg | | | |
|---|---|---|---|---|
|  | With 2,3 DPG | | Without 2,3 DPG | |
| 6 | 20.85 | 23.36 | 47.22 | 58.98 |
| 8 | 19.23 | 17.9 | 22.57 | 22.2 |
| 8.5 | 21.91 | 16.92 | 42.88 | 39.12 |
| 9 | — | — | 20.42 | 19.7 |
| 10 | 20.37 | 14.62 | 19.29 | 17.45 |

Note: The actual p50 values are half of what's listed, due to the recording software set up.

Example 3. Characterization of Nanoparticles from Example 1

$O_2$ affinity and reversible binding was characterized using a blood-gas analyzer. p50 ($O_2$ tension at $HbSO_2$=50%) was based on Hill's n (log $[HbSO_2/(1-HbSO_2)]$/log $pO_2$) and determined at 37° C. Under $pO_2$ of 720 mmHg and pH of 7.3, $HbSO_2$ was 99.99% with [log $[pO_2(7.4)]$=2.807332496; 1/k=3800.503808]; as such p50 was calculated to be 21.18 mmHg (in normal RBCs, p50 for $HbA_o$ is 26.5 and for $Hb_F$ is 20.0 mmHg).

NO scavenging and inappropriate vasoconstriction has been problematic for HBOCs and appears to increase cardiovascular complications after HBOC use. In a preliminary NO binding experiment, NO gas was bubbled through a nanoparticle suspension (RT, 15 min). UV-Vis absorbance analysis revealed no spectral peaks corresponding to the heme adduct typically observed following scavenging (Fe (II)NO, with peaks at 415, 479, 542, 610 nm).

Rheological properties of an $O_2$ carrier are critically important since the anticipated volume administered alter blood viscosity and hemodynamics. The nanoparticles' influence upon plasma rheology was studied after suspension in NZW rabbit plasma, revealing that limited effect on plasma viscosity (FIG. 3A). The minor reduction in suspension viscosity was related to the dilution of the plasma by the aqueous media of the nanoparticles. The absence of viscosity increase by the nanoparticle composition suggests that the nanoparticles do not aggregate in the presence of plasma proteins and will exert minimal influence on the rheological parameters of plasma.

Pharmacokinetic (pK) profile for the nanoparticles was determined in rats by incorporating radiolabeled Hb ($^{99m}$Tc tracer, dose 50 pCi/kg). Tracer activity was measured serially and adjusted for decay (FIG. 3B). PK parameters were determined by routine nonlinear compartmental modeling, as we have described 185. Standard two compartment modeling resulted in good fit, with distribution $t_{1/2}$=26.2±3.6 min and elimination $t_{1/2}$=300±12 min ($R^2$>0.96).

Example 4. Optimization of Nanoparticles for $O_2$ Binding/Release Characteristics Nanoparticle synthesis may be optimized for $O_2$ delivery capacity and kinetics, as appropriate to relieve tissue hypoxia in the setting of severe anemia. As noted in Example 3, nanoparticles with a p50 of 21.18 mmHg have been produced (p50 for HbAo (non-glycated hemoglobin) is 26.5; HbF (fetal hemoglobin) is 20.0 mmHg). Similarly, nanoparticles having formulations with p50 of ~20 (high affinity, current formulation), 25 (normal affinity), and 30 (low affinity) may be generated.

For example, Hb and amphiphilic polymer mixture (preloaded/not with 2,3-DPG and LMB) will undergo self-assembly in phosphate buffer (PB) at pH 7.3. [Hb] in the buffer can be titrated to different concentrations, for example between 100, 150, 200, 250 and 300 mg/mL. Nanoparticle surface chemical cross-linking can utilize Sulfo-EGS, in combination with hydroxylamine (PB buffer, pH 8.5, 5 h, 37° C.), followed by dialysis against 50 mM PB to remove the sulfo-EGS by-product. Particle size, polydispersity, and zeta potential for each nanoparticle formulation can be evaluated, as described in Example 3.

Development can be informed by an analysis of $O_2$ affinity. $O_2$ dissociation curves can be determined for each nanoparticle formulation as a function of temperature, $pCO_2$ and pH and can be referenced to values for fresh human red blood cells (RBCs) obtained from volunteers, after washing and resuspension in Krebs buffer, as described in Rogers S C, Said A, Corcuera D, McLaughlin D, Kell P, Doctor A. Hypoxia limits antioxidant capacity in red blood cells by altering glycolytic pathway dominance. $O_2$ dissociation and association hysteresis curves across the full range of gas tensions encountered in human physiology can be measured using a HEMOX analyzer as described in Guarnone R, Centenara E, Barosi G. Performance characteristics of hemox-analyzer for assessment of the hemoglobin dissociation curve. *Haematologica*. 1995; 80:426-430; p50 and cooperativity (Hill) coefficients can be calculated according to the Adair equation as described in Kobayashi M, Ishigaki K, Kobayashi M, Imai K. Shape of the haemoglobin-oxygen equilibrium curve and oxygen transport efficiency. *Respir Physiol*. 1994; 95:321-328 or Kobayashi M, Satoh G, Ishigaki K. Sigmoid shape of the oxygen equilibrium curve and the p50 of human hemoglobin. *Experientia*. 1994; 50:705-707. Nanoparticle and RBC suspensions can be matched by equimolar [Hb]. Absolute [Hb] and Hb:2,3DPG molar ratios can be manipulated to create formulations with p50 (torr) of ~20 (high affinity), 25 (normal affinity), and 30 (low affinity) for efficacy testing. The efficacy of the 2,3-DPG shuttle/reservoir can be evaluated by determining the pH-dependent shift in p50 and, if needed, PEI inner shell amine availability can be varied to maximize p50 shift between pH 7.2 (tissue) and 7.8 (lung).

Development of such nanoparticles may also be informed by measurement of $O_2$ binding-release across the full range of physiologic gas tensions. The isolated-perfused murine lung (IPL) is ideally suited to evaluate nanoparticle $O_2$ loading & unloading kinetics during perfusion at physiologically relevant rates in an intact vascular bed. The IPL can be prepared as described in Doctor A, Platt R, Sheram M L, Eischeid A, McMahon T, Maxey T, Doherty J, Axelrod M, Kline J, Gurka M, Gow A, Gaston B. Hemoglobin conformation couples erythrocyte s-nitrosothiol content to $O_2$ gradients. *Proceedings of the National Academy of Sciences*. 2005; 102:5709-5714; Maxey T S, Enelow R I, Gaston B, Kron I L, Laubach V E, Doctor A. Tumor necrosis factor-alpha from resident lung cells is a key initiating factor in pulmonary ischemia-reperfusion injury. *J. Thorac. Cardiovasc. Surg*. 2004; 127:541-547; or Zhao M, Fernandez L G, Doctor A, Sharma A K, Zarbock A, Tribble C G, Kron I L, Laubach V E. Alveolar macrophage activation is a key initiation signal for acute lung ischemia-reperfusion injury.

AJP—Lung Cellular and Molecular Physiology. 2006; 291: L1018-L1026. Nanoparticle formulations or washed human RBCs suspensions (equimolar for Hb, 2 mM) can be perfused at pulmonary transit times of 2, 4, and 8 seconds, then collected as left atrial efflux (without air exposure). Efflux gas tensions and $HbO_2$ content can be monitored (RapidLab 840 blood gas analyzer and co-oximeter, Siemens AG, GDR). $O_2$-loading rates and efficiency can be determined by perfusing deoxygenated suspensions through the lung while ventilating with 21% $O_2$, 5% $CO_2$, bal. $N_2$; $O_2$-unloading rates and efficiency can be determined by perfusing oxygenated suspensions through the lung while ventilating with 0% $O_2$, 10% $CO_2$, bal. $N_2$. Loading/unloading rates for nanoparticles with low, normal, and high p50 (as described above) can be determined and evaluated for responsiveness to pH, temperature and $pCO_2$ in comparison to values obtained for human RBCs.

Example 5. Sustenance of Nanoparticle $O_2$ Delivery by Reducing the Rate of metHb Formation Met-Hemoglobin (MetHb) accumulation during cyclic $O_2$ loading/unloading may be quantified using a thin film rotating tonometer in the presence of physiologic buffer (e.g. Krebs) or human plasma. A goal of metHb accrual may be to limit accrual to 10% following three hours of simulated circulation, with $pO_2$ cycling between 120 to 50 Torr. Nanoparticles of the disclosure comprise a reductant, and varying the molar ratio of reductant to hemoglobin (for example, between about 0.5 to about 10× molar ratios) is one means to affect metHb accrual. Samples can be obtained at time 0, 10 min, 30 min, 1 hour, 3 hours and the relative % age of oxy-, deoxy-, and metHb will be determined (RapidLab 840 blood gas analyzer and co-oximeter, Siemens AG, GDR).

Example 6. Maintenance of Sterility of Nanoparticle Formulations During Production and Prolonged Storage in Lyophilized Form Sterile production, prolonged stability of nanoparticles in a lyophilized form, and reconstituted recovery of $O_2$ binding/release properties may be demonstrated. In addition, nanoparticle aseptic filtration may be optimized. Recovery of nanoparticle functionalities (<10% change from baseline) following lyophilization and storage (up to 12 months) at 4°, 25°, and 40° C. can be confirmed.

Example 7. Evaluate and Limit Nanoparticle NO Sequestration and Vasoactivity Oxygen carrying nanoparticles of the disclosure may be optimized for minimum NO binding throughout cyclic $O_2$ loading/unloading. The rate and total NO consumption for nanoparticles formulations may be determined, employing a validated nitric oxide (NO) consumption assay. Hemoglobin payload and membrane features may be varied to limit NO sequestration to within 10% that of normal RBCs. Nanoparticles may be optimized for minimum vasoactivity throughout $O_2$ loading/unloading cycles. These experiments may correlate NO sequestration rates to vasoactivity in a standard vascular ring array (VRA), both as a function of $O_2$ content. Change in vessel tone may be benchmarked (within 10%) to values for normal RBCs to confirm that any NO trapping is below physiologically significant levels.

To further evaluate this feature, nanoparticle formulations were produced with varied hemoglobin packing and shell crosslinking (Table 2) and NO scavenging was quantified and compared to that for intact RBCs and free Hb. The results of these experiments (FIG. 4-7) demonstrate: 1) total NO sequestration by nanoparticle formulations is less than that for RBCs and free Hb and varies more so as a function of shell character and Hb packing density (FIG. 6); and 2) the rate of NO sequestration by nanoparticle formulations varies principally as a function of shell crosslinking and can be reduced below the rate for intact RBCs (FIGS. 5 and 7).

TABLE 2

| Nanoparticle formulations tested | | | |
|---|---|---|---|
| Formulation | Hb density | [Hb] (µM) | Crosslinking |
| F1 | Low | 93 | Medium |
| F2 | High | 372 | Medium |
| F3 | Medium | 170 | Low |
| F4 | Medium | 170 | High |

Example 8. Determine $O_2$-Delivery Efficacy of Nanoparticles

Demonstrating HIF-1α stabilization is the gold-standard measure of inadequate $O_2$ delivery to tissue. To accomplish this, a novel dynamic whole animal HIF-reporting model can be used to characterize the ability of oxygen-carrying nanoparticles of the disclosure to maintain tissue $O_2$ delivery during a stepwise reduction in native Hb. Normovolemic hemodilution is one means by which to simulate acute traumatic blood loss and fluid resuscitation in the field; this approach will control for hypotension, eliminating hypoperfusion it as a confounder for diminished blood $O_2$ content. Primary outcomes of interest are: 1) survival; 2) tissue $PO_2$ and 3) HIF (ODD)-luciferase signal. Means to monitor HIF expression/stabilization non-invasively during acute anemia and its resolution, by quantitating whole-animal bioluminescence in HIF-α (ODD)-luciferase mice have been described and validated. See, for example, Safran M, Kim W Y, O'Connell F, Flippin L, Gunzler V, Horner J W, Depinho R A, Kaelin W G, Jr. Mouse model for noninvasive imaging of hif prolyl hydroxylase activity: Assessment of an oral agent that stimulates erythropoietin production. *Proc Natl Acad Sci USA*. 2006; 103:105-110; or Tsui A K, Marsden P A, Mazer C D, Adamson S L, Henkelman R M, Ho J J, Wilson D F, Heximer S P, Connelly K A, Bolz S S, Lidington D, El-Beheiry M H, Dattani N D, Chen K M, Hare G M. Priming of hypoxia-inducible factor by neuronal nitric oxide synthase is essential for adaptive responses to severe anemia. *Proc Natl Acad Sci USA*. 2011; 108:17544-17549; each hereby incorporated by reference in its entirety.

As such, a stepwise increase in real-time whole body bioluminescence is observed as Hb falls; paired assessment of HIF protein levels (Western) and HIF-dependent RNA expression in multiple tissues confirm the non-invasive in vivo assessment of HIF signaling (FIG. 8). In this model, the increase in HIF-luciferase expression occurs as early as 6 hours after induction of anemia with a peak expression at ~24 hours, and is proportional to the acute decrease in Hb level and $pO_2$. As [Hb] recovers by physiological mechanism (endogenous erythropoietin) over 7 days, HIF levels return to baseline (FIG. 8E). Hypoxia exposure serves as a positive control for HIF expression in this model.

Using the HIF-1α (ODD) luciferase mouse model, the ability of oxygen-carrying nanoparticles to restore tissue $O_2$ delivery following reduction in native [Hb] may be characterized. An exchange transfusion may be performed with nanoparticles (normalized total hemoglobin) or pentastarch (normovolemic anemia, control) to study $O_2$ delivery+/- hypoxic stress by in vivo bioluminescent imaging and tissue oxyphor quenching. In a separate hemodilution group, hemoglobin may be normalized by re-infusing shed murine RBCs to establish reference HIF-luciferase and oxyphor activity; Nanoparticles quenching may be within 10% that achieved by re-infusing murine RBCs. Pharmacokinetics (PK) of the nanoparticles particle may also be determined. Nanoparticles may be labeled with $^{99m}$Tc and administered as described above. Activity may be measured serially, and PK parameters may be calculated. 75% retention may be expected at 3 hours, with duration of circulation matched to duration of efficacy using HIF-luciferase and oxyphor quenching.

Example 9. Evaluation of Nanoparticle Efficacy in a Rodent Hemorrhagic Shock Model Polyethyleneimine polymers were grafted with hydrophobic alkyl groups by covalent means. Palmitic acid was activated with the carbodiimide EDAC (1-ethyl-3-(3-dimethylaminopropyl) carbodiimide, hydrochloride) followed by addition of the polymer to achieve greater than 50% functionalization of free primary amine groups and a partial functionalization of the secondary amines. The amphiphilic polymer was dispersed in anhydrous chloroform and gently vortexed for 2-5 minutes. The measurement of hydrodynamic diameter of this construct confirms the formation of a 7-10 nm sized unimolecular inverted micellar (IM) structure.

Concentrated and purified hemoglobin and 2,3-DPG mixture, and methylene blue were suspended in aqueous medium and was added to the organic solvent mixture of the IM. This bi-phasic mixture was allowed to settle down and inverted several times until the all the payloads were transferred to the organic layer comprising of IMs. The transfer can be achieved by briefly shaking/swirling and inversion or a combination method. Hemoglobin was human hemoglobin extracted and purified from expired RBCs. Hemoglobin was stabilized as carboxyhemoglobin (HbCO), purified via ion-exchange chromatography, and concentrated using ultrafiltration to 4.0 g/dL, The concentration of hemoglobin used to generate the nanoparticles was 10 mg/mL. The concentration of 2,3-DPG was 10 mg/mL. The concentration of leucomethylene blue was 5 mg/mL. The payload-incorporated IM was transferred to a long neck glass tube and to this equal volume of nanopure water (0.2 uM) was added. The mixture was briefly sonicated for 1-2 min followed by a slow evaporation of the organic solvent under reduced pressure following a reverse phase solvent evaporation protocol. The removal of organic solvent was confirmed by the prolonged rotary evaporation and dialysis. In a typical preparation, nanoparticles comprised an average of 4000 hemoglobin molecules per nanoparticle. Following the self-assembly and reverse phase solvent evaporation, the nanoparticles were subjected to surface chemical cross-linking using Sulfo-EGS (ethylene glycol bis[sulfosuccinimidylsuccinate], PBS, pH 8.5) in combination with hydroxylamine for 5 h at 37° C. The intramolecular crosslinking step is devoid of use of any chemical crosslinker. Nanoparticle sizes, shape, and morphology were measured by TEM, DLS, and AFM among other methods. Nanoparticles had a hydrodynamic diameter of 150-180 nm, or 173±10 nm after re-suspension, with polydispersity of 0.26±0.01, and zeta potential of ~12±2 mV. Crosslinking has limited effect on particle size and zeta potential: 167±56 nm, +7±2 mV, respectively. Assays were performed as described in Pan D, Caruthers S D, Hu G, Senpan A, Scott M J, Gaffney P J, Wickline S A, Lanza G M. Ligand-directed nanobialys as theranostic agent for drug delivery and manganese-based magnetic resonance imaging of vascular targets. J Am Chem Soc, 2008; 130: 9186-9187.

Example 10. Evaluation of Nanoparticle Efficacy in a Rodent Hemorrhagic Shock Model Nanoparticle efficacy was evaluated in a rodent hemorrhagic shock model. Nanoparticles were produced as described in Example 9. Rats (Sprague Dawley, 400 g, N=3) were anesthetized (isoflurane) and underwent tracheotomy with institution of mechanical ventilation (RA) and cannulation of the jugular and femoral veins and the carotid and femoral arteries. After establishing baseline values for blood $O_2$ content and AV $O_2$ difference, 25% blood volume was removed, new values were obtained, and animals were resuscitated with an equal volume of the blood substitute (N=2) or normal saline (N=1). Nanoparticles (NP) were suspended at 40 wt/vol %, with suspension [Hb] of 4 mM. FIG. 9 shows the outcome of the experiment. The plot illustrates an expected, striking increase in the AV 02 difference with blood removal (rising from 24 to 67%), that (A) persisted following resuscitation with normal saline and (B) resolved following resuscitation with the blood substitute (normalizing from 67 to 31%). In (C), a difference was not observed in the hemodynamic effect afforded by either resuscitation fluid, suggesting that the benefit in $O_2$ delivery from the blood substitute arises from improved $O_2$ content, in addition to restoration of blood pressure. Moreover, unlike other hemoglobin-based blood substitutes, which are known to cause vasoconstriction and hypertension from NO sequestration; the NP-based blood substitute reconstituted normal hemodynamics. This further supports the in vitro data that the NP does not induce significant NO sequestration.

Example 11. Preparation of Nanoparticles

A mixture of hemoglobin (Hb) and amphiphilic polymer mixture (preloaded/not with 2,3-DPG and LMB) underwent self-assembly in phosphate buffer (PB) at pH 7.3 using a microfluidization/homogenization technique. The mixture was vigorously vortexed to homogeneity followed by continuously processing thereafter at 18000 psi for 4 min with an LV1 Microfluidics emulsifier. [Hb] in the buffer can be titrated to different concentrations, for example between 100, 150, 200, 250 and 300 mg/mL. Nanoparticle surface chemical cross-linking can utilize Sulfo-EGS, in combination with hydroxylamine (PB buffer, pH 8.5, 5 h, 37° C.), followed by dialysis against 50 mM PB to remove the sulfo-EGS by-product. Particle size, polydispersity, and zeta potential for each nanoparticle formulation can be evaluated as described earlier. The full preparation was dialyzed (100 kD membrane) against infinite sink of PBS. The nanoparticles (NP) were collected and tested for free Hb using the Drabkins reagent.

To dialyze against PBS, any suitable dialysis system may be used. Although the procedure is described for the Float-A-Lyzer G2 device, alternative systems are known in the art. To pre-wet the membrane, glycerin was removed to achieve maximum membrane permeability following this soaking procedure. Briefly, the cap was unscrewed at the top of the device, the device was filled with 10% ethanol (EtOH)

solution (in ddH$_2$O), the cap replaced, and then the body of the Float-A-Lyzer G2 was threaded through the hole in the flotation ring and the ring was snugly pulled up beneath the collar of the top piece. The device+floatation ring was placed in an 80 ml beaker filled with 70 ml of 10% EtOH solution for 10 minutes with stirring at 300 rpm. The device+floatation ring was removed from the beaker, the floatation ring removed and the cap unscrewed to aspirate out the EtOH inside the device. Any remaining drops of EtOH were removed by inverting the device and shaking. Next, the device was flushed thoroughly with deionized (DI) water, and then filled with DI water and re-capped. The capped device was placed in the floatation ring, and then the device+floatation ring was placed in a beaker with 70 ml DI water for 15 minutes with stirring at 300 rpm. The water was removed as described above for the EtOH. The device was flushed again with DI water and excess water removed by gentle inversion and shaking.

After pre-wetting the Float-A-Lyzer G2, the membrane was conditioned with the dialysate buffer by rinsing the inside of the membrane several times with PBS. Excess buffer was removed, and the device was loaded with 900 ul of the nanoparticle preparation. The device was placed in the floatation ring and then dialyzed in 70 ml of PBS for 20 minutes at room temperature with stirring at 300 rpm. The device was removed from the dialysate after 20 minutes.

Following dialysis, the 25 ml volume of dialysate was concentrated using an Amicon Ultra 15 Centrifugal filter, which was washed in ddH$_2$O prior to use. Briefly, the Amicon Ultra filter was washed by adding 15 ml of ddH$_2$O to the top cassette. The filter was centrifuged at 3400×g for 60 minutes and 4° C. Once spun, the cap was removed and the flow through at the bottom of the conical and any liquid remaining in the top cassette was discarded. 15 ml of the dialysate was added to the cassette and centrifuged at 3400×g for 30 minutes and 4° C. After 30 minutes another 10 ml of dialysate was added to the filter, and the filter was again centrifuged at 3400×g for an addition 60 minutes at 4° C. Once it has finished spinning, the solution was removed from the filter cassette using a 200 ul pipette. This solution will contain the concentrated Hb. If the amount of solution is greater than 1.3 ml, spin for a longer period of time. Once the 25 ml volume of dialysate has been concentrated to less than 1.3 ml, remove the solution from the cassette with a 200 ul pipette and dilute it to a 1.3 ml total volume using PBS.

To test for free Hb, a Drabkin's assay was run on the sample using a 1:1 dilution with Drabkin's reagent following Manufacturers protocol. 300 ul of solution was added to each well (in triplicate) and the absorbance of cyanomethemoglobin was recorded at a fixed wavelength (540 nm). The hemoglobin concentration of the original hemoglobin solution was measured using the following equation: Heme (mM)=(sample absorbance @ 540 nm×dilution factor) (Extinction coefficient @540 nm×path length correction); Dilution; factor=2; Extinction coefficient=11 mM$^{-1}$cm$^{-1}$; Path length correction=0.8 for 300 μl in the 96 well plate; For Hb tetramer, the answer was divided by 4.

What is claimed is:

1. A method for providing oxygen to an organ ex vivo, the method comprising perfusing an organ with an effective amount of an oxygen-carrying nanoparticle, wherein the nanoparticle has a substantially bi-concaved disc shape and comprises an aqueous core, a bi-layered shell comprising an amphiphilic polymer, and a payload; and wherein the bi-layered shell has a hydrophilic outer layer, a hydrophilic inner layer, and a hydrophobic region between the hydrophilic outer layer and the hydrophilic inner layer;

the amphiphilic polymer comprises a branched, amine-containing polymer linked to a lipid; and the payload comprises an oxygen-carrying agent, an allosteric effector, and a reducing agent.

2. The method of claim 1, wherein the amphiphilic polymer comprising the hydrophilic outer layer of the shell is derivatized with polyethylene glycol, such that the particle has a zeta potential of about −15 mV to about +15 mV.

3. The method of claim 1, wherein the average diameter of the nanoparticle is from about 150 nm to about 300 nm, and the average height of the nanoparticle is from about 30 nm to about 80 nm.

4. The method of claim 1, wherein the oxygen-carrying agent is synthetic hemoglobin or naturally occurring hemoglobin.

5. The method of claim 1, wherein the allosteric effector is selected from the group consisting of 2,3-diphosphoglycerate (2,3-DPG), inositol hexaphosphate (IHP), pyridoxal-phosphate (PLP), and 2-[4-[[(3,5-dimethylanilino carbonyl] methyl]-phenoxy]-2-methylpropionic acid.

6. The method of claim 1, wherein the reducing agent is selected from the group consisting of leucomethylene blue, glutathione and ascorbate.

7. The method of claim 1, wherein the nanoparticle comprises about 3000 to about 10,000 hemoglobin molecules.

8. The method of claim 1, wherein the nanoparticle comprises about 20% to about 60% (w/v) hemoglobin or about 30% to about 60% (w/v) hemoglobin.

9. The method of claim 1, wherein the nanoparticle limits the oxidation of hemoglobin to about 10% or less of the total concentration of hemoglobin in the nanoparticle.

10. The method of claim 1, wherein the branched, amine-containing polymer is selected from the group consisting of a polyethyleneimine branched polymer, a PAMAM dendrimer, a star polymer, and a graft polymer.

* * * * *